United States Patent
Callicrate et al.

(10) Patent No.: US 9,271,735 B2
(45) Date of Patent: Mar. 1, 2016

(54) METHOD AND SYSTEM FOR LIGATING A BODY PART

(75) Inventors: Michael P. Callicrate, St. Francis, KS (US); Roy Allen Harbach, Highlands Ranch, CO (US)

(73) Assignee: NO-BULL ENTERPRISES LLC, St. Francis, KS (US)

( * ) Notice: Subject to any disclaimer, the term of this patent is extended or adjusted under 35 U.S.C. 154(b) by 691 days.

(21) Appl. No.: 13/583,939

(22) PCT Filed: Mar. 14, 2011

(86) PCT No.: PCT/US2011/028312
§ 371 (c)(1),
(2), (4) Date: Nov. 21, 2012

(87) PCT Pub. No.: WO2011/113040
PCT Pub. Date: Sep. 15, 2011

(65) Prior Publication Data
US 2013/0226202 A1    Aug. 29, 2013

Related U.S. Application Data

(60) Provisional application No. 61/313,585, filed on Mar. 12, 2010, provisional application No. 61/367,198, filed on Jul. 23, 2010, provisional application No. 61/441,943, filed on Feb. 11, 2011.

(51) Int. Cl.
*A61B 17/10* (2006.01)
*A61B 17/08* (2006.01)
*A61B 17/12* (2006.01)

(52) U.S. Cl.
CPC ..... *A61B 17/12009* (2013.01); *A61B 17/12013* (2013.01); *A61B 2017/12018* (2013.01)

(58) Field of Classification Search
CPC ................ A61B 17/12009; A61B 17/12013; A61B 2017/12018
See application file for complete search history.

(56) References Cited

U.S. PATENT DOCUMENTS

| 4,009,509 A | 3/1977 | McCormick |
| 4,033,352 A | 7/1977 | van Reenen |
| 4,691,704 A | 9/1987 | Wadsworth |
| 5,188,637 A | 2/1993 | Wadsworth |
| 5,236,434 A | 8/1993 | Callicrate |
| 5,282,825 A | 2/1994 | Muck et al. |
| 5,383,882 A * | 1/1995 | Buess et al. ................ 606/157 |
| 5,403,325 A | 4/1995 | Callicrate |
| 5,417,684 A | 5/1995 | Jackson et al. |
| 5,425,736 A | 6/1995 | Wadsworth |
| 5,445,167 A | 8/1995 | Yoon et al. |

(Continued)

OTHER PUBLICATIONS

Official Action for U.S. Appl. No. 13/046,392, mailed Apr. 30, 2013 7 pages Restriction Requirement.

(Continued)

*Primary Examiner* — Julian W Woo
(74) *Attorney, Agent, or Firm* — Sheridan Ross P.C.

(57) ABSTRACT

A ligature device and method of use are disclosed. More specifically, a ligature device capable of maintaining a ligature band in an elongated position, applying a preformed ligation band to an object to be ligated, manually releasing the ligation band from an elongated position, and securing a ligation band in a tensioned position is described. The ligation device may be used to apply ligation bands to various body parts of various animals.

16 Claims, 17 Drawing Sheets

(56) References Cited

U.S. PATENT DOCUMENTS

| | | |
|---|---|---|
| 5,517,728 A | 5/1996 | Woods |
| 5,675,870 A | 10/1997 | Cooper |
| 5,681,329 A | 10/1997 | Callicrate |
| 5,693,059 A | 12/1997 | Yoon |
| 5,722,123 A | 3/1998 | Davignon et al. |
| 5,810,845 A | 9/1998 | Yoon |
| 5,843,095 A | 12/1998 | Callicrate |
| 5,855,586 A * | 1/1999 | Habara et al. ............ 606/144 |
| 5,902,309 A | 5/1999 | Wadsworth |
| 5,997,553 A | 12/1999 | Callicrate |
| 6,270,507 B1 | 8/2001 | Callicrate |
| 6,409,738 B2 | 6/2002 | Callicrate |
| 7,017,237 B2 | 3/2006 | Magno, Jr. |
| 7,371,242 B2 | 5/2008 | Wadsworth et al. |
| 8,118,819 B2 | 2/2012 | Miyamoto et al. |
| 2003/0236541 A1 | 12/2003 | Callicrate et al. |
| 2005/0080433 A1 | 4/2005 | Porter |
| 2007/0062012 A1 | 3/2007 | Caison |
| 2007/0234524 A1 | 10/2007 | Witt |
| 2008/0255614 A1 | 10/2008 | Menoudakos |
| 2011/0224695 A1 | 9/2011 | Callicrate et al. |

OTHER PUBLICATIONS

Official Action for U.S. Appl. No. 13/046,392, mailed Jul. 26, 2013 11 pages.
Official Action for Australia Patent Application No. 2011226642, dated Jun. 14, 2013 4 pages.
Official Action for Canadian Patent Application No. 2,792,907, dated Aug. 22, 2013, 3 pages.
Notice of Allowance for U.S. Appl. No. 13/046,392, mailed Dec. 10, 2013. 13 pages.
International Search Report for International (PCT) Patent Application No. PCT/US2011/028312, mailed Jul. 22, 2011 3 pages.
Written Opinion for International (PCT) Patent Application No. PCT/US2011/028312, mailed Jul. 22, 2011 5 pages.
International Preliminary Report on Patentability for International (PCT) Patent Application No. PCT/US2011/028312, mailed Sep. 27, 2012 7 pages.
Official Action for U.S. Appl. No. 13/046,392, mailed Oct. 25, 2012 6 pages Restriction Requirement.

* cited by examiner

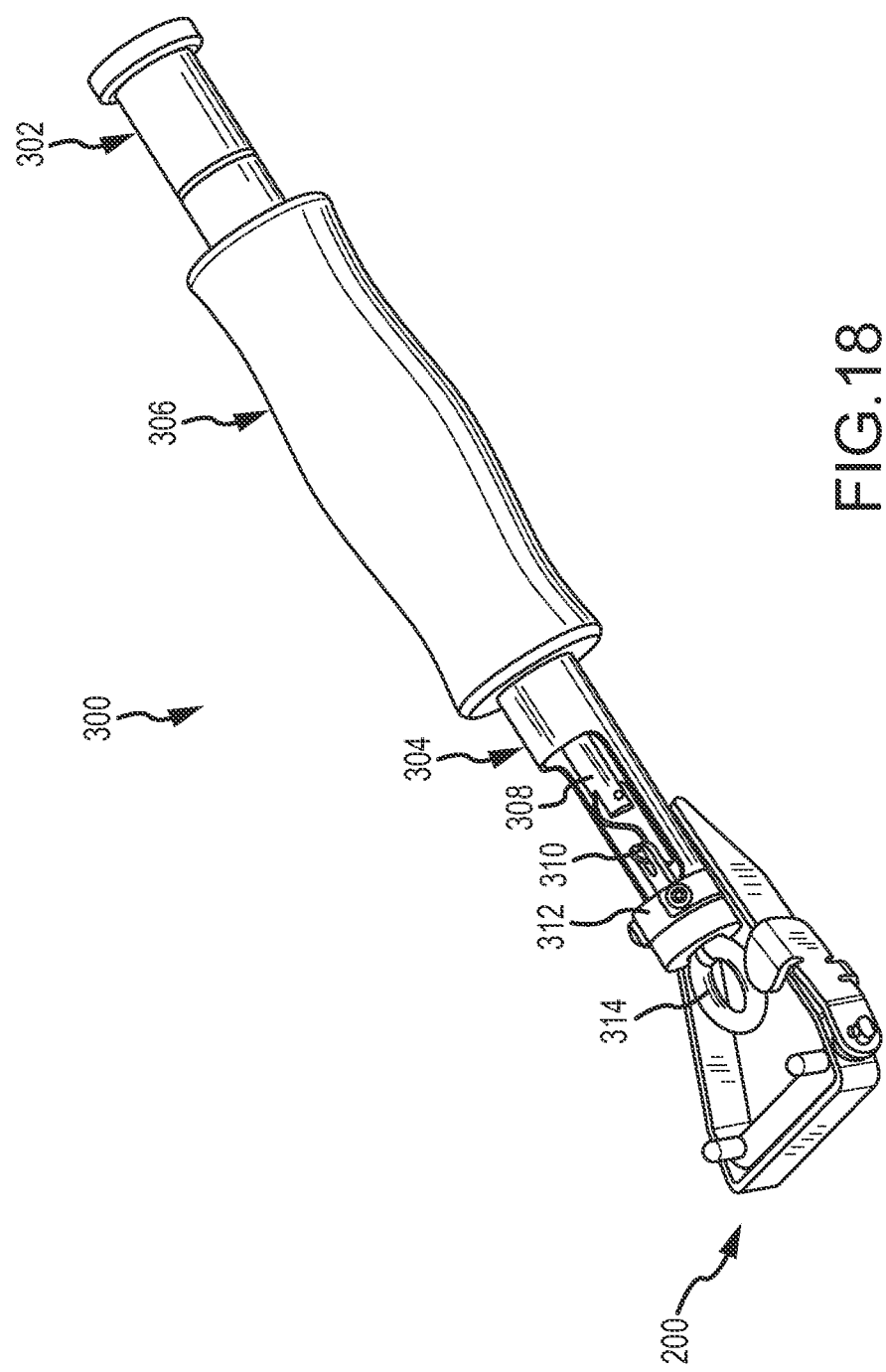

METHOD AND SYSTEM FOR LIGATING A BODY PART

CROSS REFERENCE TO RELATED APPLICATION

This application is a national stage application under 35 U.S.C. 371 of PCT Application No. PCT/US2011/028312 having an international filing date of Mar. 14, 2011, which designated the United States, which PCT application claimed the benefit of U.S. Application Ser. No. 61/313,585, filed on Mar. 12, 2010 and of U.S. Application Ser. No. 61/367,198, filed on Jul. 23, 2010 and of U.S. Application No. 61/441,943, filed on Feb. 11, 2011, all of which are incorporated by reference in their entirety.

FIELD OF THE INVENTION

The present invention relates generally to ligature tools and devices. More specifically, the present invention relates to methods and tools useful for ligating a body part of an animal using ligation members acting in tension and an application tool.

BACKGROUND OF THE INVENTION

A preferred method for the removal of a body part is ligation. Ligation is a process in which a band or chord is fastened to a body part to be removed in order to constrict it, thus cutting off the supply of blood and systematic support. The body part thereafter atrophies and drops away from the body. Ligation is used for many purposes including castration and removal of horns, tails or other body parts from animals.

Ligation has a number of advantages over surgical procedures for such applications. First, ligation has a safety advantage in that the animal normally does not become susceptible to infection. For example, in the case of castration of bulls, a period of about two weeks to a month typically passes between the time that the ligature is attached to the scrotum and the time that the scrotum drops off. During this time the area adjacent to the ligature heals, thus reducing the likelihood of infection. Another advantage of ligation is that ligation can be performed critically by non-expert personnel, thereby reducing costs. In addition, when the ligature is sufficiently tight, ligation can generally be performed with little stress on the animal because the body part numbs quickly after the blood supply is cut off.

Known ligation devices for use with the younger male animals include elastrator rings. Elastrator rings may be applied to an animal with the use of a scissor like instrument capable of expanding a rubber ring which may then be placed in a desired position, the handles released, and the tool withdrawn. Elastrator rings may suffer from drawbacks of supplying insufficient or excessive tension to a body part. Insufficient tension may result in unsuccessful ligation in addition to infliction of pain upon the animal, thus frustrating the purpose of ligation. Known elastrator rings, while broadly used around the world due to their inexpensive cost, are considered one of the most stressful procedures an animal can experience.

Another ligation method is disclosed in U.S. Pat. No. 4,691,704 to Wadsworth, which is hereby incorporated by reference in its entirety. A loop of a ligature elastomeric band is formed around the body part to be ligated, and then an end portion of the band is attached to a tightening rod. The tightening rod can then be retracted in a substantially linear fashion by successive pulls on a trigger mechanism, thereby tightening the loop. However, the process of tightening the loop through successive pulls on the trigger mechanism is time consuming and the animal must therefore be restrained for a relatively long period of time. In addition, the tension which can be imparted to the band, and the tightness of the loop, are limited by the hand strength of the user, the length of the rod, etc. Moreover, relatively large frictional and abrasive forces are exerted on the band where the band is attached to the tightening rod, thereby increasing the likelihood of damage to the elastomeric material, causing breakage before the desired tension is achieved. Additionally, due to the design of the ligature tool, an operator is limited in the extent to which the band can be tightened. Once an operator has fully retracted the tightening rod, the loop's tightness cannot be increased.

Another method of ligation is disclosed in U.S. Pat. No. 5,236,434 to Callicrate. Callicrate discloses a method and apparatus for ligation including the steps of forming a loop about the body part with a band of ligature material and winding the band to tighten the loop. The band may be tightened by securing the band to a spool and then rotating the spool to align the band. After the loop is tightened the loop can be secured by crimping a grommet so that the band is secured therein.

It is known in the art that proper and successful ligation often requires a sufficiently precise amount of tension to be applied to a band. The application of excessive tension may cause the band or device being applied to break. Conversely, when inadequate tension is applied, ligation efforts may prove unsuccessful, subject an animal to pain, and often result in a user resorting to conventional and less desirable methods of surgical castration.

Prior art devices that employ an endless loop or band are known to provide flexibility in that they may accommodate a variety of different sized body parts and different amounts of tension. However, it is known that such devices require cutting or severing of at least a portion of the band after tension is applied. This cutting may result in various complications, including breakage of the band, and gaps being formed between a band and a band clamp. Moreover, provision of a sharp cutting tool, whether or not associated with a ligation tool, is inherently dangerous and can result in undesired harm to an operator. Prior art devices which require separate cutting tools for performing ligation procedures may frustrate ligation procedures or place a user in harm's way when such a tool is misplaced or forgotten.

SUMMARY OF THE INVENTION

Accordingly, there exists a long-felt but unmet need to provide a cost-efficient and humane device for the ligation of body parts of young animals. There further exists a need to provide a device that limits a user's discretion or ability to apply tension to a certain limit or to a range of discrete forces and which further does not require a user to cut a band after tension has been applied.

These and other needs are addressed by the various embodiments and configurations of the present invention. Late stage castration is known to often be desirable, as methods such as surgical castration and elastrator rings may often result in reduction of testosterone levels and/or an animal's appetite or ability to gain weight when applied to very young animals. Methods of providing artificial or unnatural hormones are becoming less desirable due to costs, health benefits of natural meat, and other concerns. Additionally, various dangers and complications are known to exist when, for example, ligation efforts fail on a 2,500 pound bull. If a partially or fully applied ligature band breaks due to complications in cutting a band or over-tightening a band, blood flow and sensation may quickly return to such an animal causing complications requiring professional assistance to prevent death or other trauma. Known devices do not currently exist for appropriately applying a tensioned band to young animals. Accordingly, it is an object of the present invention to provide a user with the option of ligating/castrating a younger animal without the previously mentioned complications associated with surgical castration and elastrator rings.

By way of providing additional background, context, and to further satisfy the written description requirements of 35 U.S.C. §112, the following references are hereby incorporated by reference in their entireties: U.S. Pat. No. 4,033,352 to van Reenen, U.S. Pat. Nos. 4,691,704, 5,425,736, 5,902,309, 7,371,242, and U.S. Patent Application Publication No. 2004/0158265 to Wadsworth, U.S. Patent Application Publication No. 2005/0080433 to Porter, U.S. Pat. Nos. 5,236,434, 5,403,325, 5,681,329, 5,843,095, 5,997,553, 6,270,507, 6,409,738, U.S. Patent Application Publication No. 2003/0236541 to Callicrate, and U.S. Patent Publication Nos. 2005/0080433 to Porter, and 2004/0158265 to Wadsworth et al.

It is an object of the present invention to provide a cost effective, manual and/or power source operable device that allows a user to place a band or elastic member around a body part and then selectively apply a desired amount of tension upon the band once formed around the body part, without the need for a sharp cutting tool to complete the procedure. This may be accomplished by, for example, a manually operable mechanism that a user may exert a force upon, which is connected to one end of a band to be applied, and which may further draw the band through a clasp or crimp band, thus decreasing the circumference of a ligature band and increasing tension on a body part. The tightened band is then released from the tool without a cutting step.

It is yet another object of the present invention to provide a ligation device for young animals and that is further capable of accommodating and applying a plurality of different size and strength bands to a body part. Different size and strength bands, according to various embodiments, may be utilized on different aged, sized, breed, body part, etc. of an animal.

It is yet another object of the present invention to provide a ligation/castration system and method where a ligation tool and corresponding deployable loop or ring for positioning on and/or around a body part, thus allowing for the entire loop or ring and body part to drop away from an animal once ligation is completed and avoiding the need to sever a portion of the band/loop once tightened. In one embodiment, this may be accomplished, at least in part, by a device that allows for simple manual segregation of a loop or ring from various aspects of a tool. Accordingly, in various embodiments, the present invention does not require a user to cut or sever a portion of a ligation band after tension is applied as in currently known devices and methods.

Those of skill in the art will recognize that various complications may arise due to cutting of ligation bands. If cutting of a band is not conducted properly, ligation efforts may fail and result in a need to resort to more traditional castration methods or injury to the animal and/or user. The present invention therefore contemplates a device and band where the band may remain on an animal after tensioning and crimping procedures are conducted and that further does not require cutting procedures or devices. Crimping procedures of the present invention may include various adjustable devices disposed on a portion of a ligature band. Adjustable devices of the present invention may include, by way of example and not limitation, various compressible or malleable clips, bands, screws, bolts, thumb-screws, zip-ties, conventional cords and cables, rings, staples, and other fasteners capable of achieving and/or securing tension in a ligature band. Thus, in various embodiments, devices and methods are provided which do not require the use of cutting tools or processes and therefore significantly simplify and advance the process of ligation.

In one embodiment, a pre-formed adjustable ligation band is provided. For example, a ligating band is provided that is comprised of:
(a) a defined length of ligature material folded at a midpoint to create a loop and secured at the non-loop end with a device that receives tension and maintains the ligature material in a loop;
(b) a crimping band disposed around a portion of the ligature material that, when in a crimped state, secures tension around a part to be ligated; and
(c) a device for selectively securing the crimping band in a first position when in an un-crimped state.

In one embodiment, pre-formed adjustable ligation bands are provided in a magazine or dispensing device, thereby confining ligation bands to a relatively small space and facilitating the application of multiple ligation bands to one or more animals.

In another embodiment, a crimping band is notched or similarly shaped to provide for nesting of the crimping band within a portion of a ligation tool and eliminating unwanted float or movement of the crimping band therein. In an alternative embodiment, crimping bands comprise a specific size and shape which ensures their proper use with the proper corresponding tool. For example, a ligation band for use on a young bull may comprise a crimping band with a specific and unique shape such that it only fits and is capable of use with the ligation tool that corresponds (e.g. applies the proper tension) to such an animal.

Mechanisms of the present invention for applying tension to a band may be comprised of any number of devices. For example, a tightening rod with a grip suitable for communication with a user may be provided. Tightening rods of the present invention may be suitable for the linear application of tension force. In one embodiment, a user may grasp and/or stabilize a main portion of a ligation tool while simultaneously imparting tension upon a tightening rod, which may increase the tension on a ligature band. Alternatively, one or more tightening levers may be provided. Portions of ligation bands may be attached or connected to one or more tightening levers which may assist in the displacement of at least a portion of a band from a substantially non-tensioned state to a tensioned state.

In alternative embodiments, a winding mechanism or ratcheted device is provided which is capable of interfacing and/or applying tension to a band. Where a portion of a band is wound around a tightening object, it will be recognized that the band may be unwound or similarly released from a tension applicator (without employment of a cutting mechanism) once a portion of the band has been crimped or otherwise secured around an animal part.

In additional alternative embodiments, application of tension force to a ligature band is accomplished through various power assisted devices. For example, various motors, such as servo-motors, Brushless Direct Current Motors, Alternating Current Motors, and various other similar devices may be incorporated within various aspects of the present invention which may be capable of applying a precise and sufficient amount of tension to a ligature band with minimal user effort (e.g. through the push of a button). The present invention further contemplates the ability to interconnect with known devices which may already incorporate these devices. For example, embodiments of the present invention may be connected to electric drills, pneumatic systems, Dremels®, and other tools. Batteries, solar power, and various other energy sources can also provide desired power for driving features of the present invention.

Alternatively, aspects of the present invention may include the ability to communicate with a compressor or similar energy generation/storage device that may assist in the application of force to a band. Various embodiments of the present invention include the ability to receive, for example, pressurized air which may be capable of exerting a force (e.g. via a pressure chamber) that expands an elastic band.

It is yet another object of the present invention to provide a ligation device that limits a user's discretion as to the amount of tension that may be applied to a body part. For example, an indicator may be provided to display the proper amount of displacement of one or more mechanisms of the device. Additionally, indicators such as stop pins and similar devices may operate to fix a mechanism in a desired position once proper tension is achieved. Alternatively, indicators may simply provide feedback on displacement and tension, while additional mechanisms may be activated to fix one or more members of the device in a given position. For example, tension indicators as described in U.S. Pat. No. 6,409,738 to Callicrate, which is hereby incorporated by reference in its entirety, may be incorporated into various aspects of the present invention. Similarly, other known devices, such as strain gauges, colored indicators, various devices useful for indicating a level of tension, and combinations thereof may be incorporated into features of the present invention.

While tension gauges are known in the prior art, there still exits a problem in that operators my disregard such gauges, wrongly thinking that greater tension is always preferable. Excessive tension, however, may result in the breakage of a band, undesired pain to an animal, problems in repeating the ligation, loss of time, opportunities, etc. Accordingly, various physical and mechanical aspects of the present invention are provided that may limit or dictate a specific amount or range of tension which is to be applied to a ligature band. In one embodiment, the present invention comprises a tension rod which may only extend to a predetermined limit, thus limiting the amount of tension a user may apply to a ligation band.

It is yet another object of the present invention to eliminate, reduce, or minimize various complications associated with ligating animals. For example, it is an object of the present invention to reduce the number of failed ligation attempts, either due to over-tightening or under-tightening of ligation bands. Additionally, the present invention contemplates the reduction of complications associated with gaps in ligation bands or inadequate encapsulation of a body part during ligation.

In various embodiments, a ligation tool and associated band is provided wherein crimping is not required to secure tension in an installed band. Instead, a locking or ratcheting system is provided comprising a ligation band, a linkage or pull tang, and a collar having an opening therethrough. The linkage is secured to the ligation band and is adapted for connection with a tightening rod, human hand, or similar device. The collar includes one or more locking mechanisms that allow the ligation band to pass or translate through a portion of the collar but prevents reverse translation, thus permitting the tightening of the ligation band while maintaining the tension therein.

In one embodiment, a collar comprises a plurality of teeth through which the linkage or tang may pass. As tension is applied to the linkage, the ligation band is translated through an opening of the collar and contacts the teeth. As translation occurs, the teeth engage the band and prevent reverse translation thereof. In alternative embodiments, a locking mechanism is provided comprising a pivotable pawl, as shown by U.S. Patent Application Publication No. 2007/0234524 to Witt, U.S. Pat. No. 7,017,237 to Magno, Jr., and U.S. Pat. No. 4,009,509 to McCormick; a flexible pawl, as shown by U.S. Pat. No. 5,675,870 to Cooper; an angled locking surface, as shown by U.S. Pat. No. 5,722,123 to Davignon et al.; or an insertable barb, as shown by U.S. Pat. No. 5,517,728 to Woods; all of which are hereby incorporated by reference in their entireties.

In alternative embodiments, a locking or ratcheting system is provided wherein interaction occurs between an elastic band and a collar portion such that tension is maintained in the band as it applied, without the need to perform additional tension-securing step and/or a cutting step in order to secure the band in its final position for ligation. In various embodiments, an elastomeric member is provided in a loop or circular arrangement with a substantially non-elastic tang portion attached thereto. A collar portion is further provided, the collar portion having an aperture through which the tang and at least a portion of the elastomeric loop may be disposed. Therefore, in at least some embodiments, an elastomeric band may be tightened around an object by applying a force to the tang portion and maintaining the collar portion in a generally fixed position relative to the tang and the elastomeric band. As tension is applied to the band, features of the collar portion, such as protrusions, teeth, wedge portions, and similar features secure tension is the band as the band is passed therethrough.

In a preferred embodiment, bands of the present invention are adapted for use in ligating one or more parts of animal. However, it is contemplated that bands of the present invention may be used in a variety of applications, related and unrelated to ligation procedures. For example, bands of the present invention, particularly bands comprising locking means or locking mechanisms, are suitable for use in securing bags, such as known garbage bags, red-bags (hazardous waste), etc. Additionally, it is contemplated that bands of the present invention may be employed in a wide variety of medical applications, including tourniquet procedures, arterial clamping, etc. In alternative embodiments, a band comprising reversible locking features may be employed to secure laces and tensioning members on clothing, jackets, shoes, etc. Accordingly, it will be recognized that bands of the present invention are not limited to use in a particular application and may be employed in myriad applications and devices where tensioning an elastic member, either reversibly or irreversibly, is desirable.

In another embodiment, a locking mechanism comprises biasing members disposed within a collar opening. The biasing members allow motion of the ligation band through the opening in a tightening direction. However, upon opposing motion of the ligation band, the biasing members bear against the surface of the ligation band and produce a wedging action that binds the ligation band in the opening and prevents any further backward motion. The biasing members may include ridges, protrusions, pawls, hooks, or barbs. To optimize performance, the biasing members may be spring loaded to increase the binding motion of the biasing member. Additionally, high friction materials may be used to increase the friction between the biasing members and the ligation band. An advantage of this embodiment is that the ligation band and the linkage are toothless, thus reducing the cost and complexity of the deployable ligation assembly.

In yet another embodiment, the locking mechanism comprises locking members disposed within the collar opening and ridges disposed on the linkage. The locking members and ridges provide 360 degree engagement, thus increasing the securing force of the locking mechanism. The locking members may include ridges, protrusions, hooks, or barbs.

One advantage of a ligation device employing a locking mechanism is the ability to remove the crimping assembly, including associated levers and linkages. First, removal of the crimping assembly reduces the weight and the overall size of the ligation device, thus making it easier to use. Second, it is known that complications may arise where improper or inadequate crimping occurs. For example, known crimping devices and methods may leave a gap between ends of a loop or similarly may result in an overhang or protrusion of a metal clip into a ligation area or circumference. These results can lead to infliction of pain and/or harm to an animal and unsuccessful ligation.

In certain embodiments, a ligation tool and associated band is provided wherein crimping is required to secure a tightened ligation band. The ligation tool is designed to reduce the complications associated with gaps in ligation bands or inadequate encapsulation of a body part during ligation. In one embodiment, a malleable collar is provided that has an opening configured to allow passage of a linkage and an associated ligation band. Once a desired level of tension is achieved in the ligation band, a crimping force is applied to the malleable collar. The crimping force deforms the malleable collar, thus securing the linkage and ligation band in place.

In various embodiments, a pre-tensioning device is provided to assist a user in placement of a ligation band around a body part. Where provided, the pre-tensioning device is either permanently attached to the ligation device or temporarily secured to the ligation device. Additionally, in various embodiments, tension indicators are provided to indicate a desired level of tension to be applied to the ligation band, including protrusions and/or extensions provided along a length of a tightening rod, visual indicators, and/or tension sensing means.

BRIEF DESCRIPTION OF THE DRAWINGS

FIG. 18 is a perspective view of a ligation band application tool according to one embodiment of the present invention;

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION OF PREFERRED EMBODIMENTS

Figure 1:
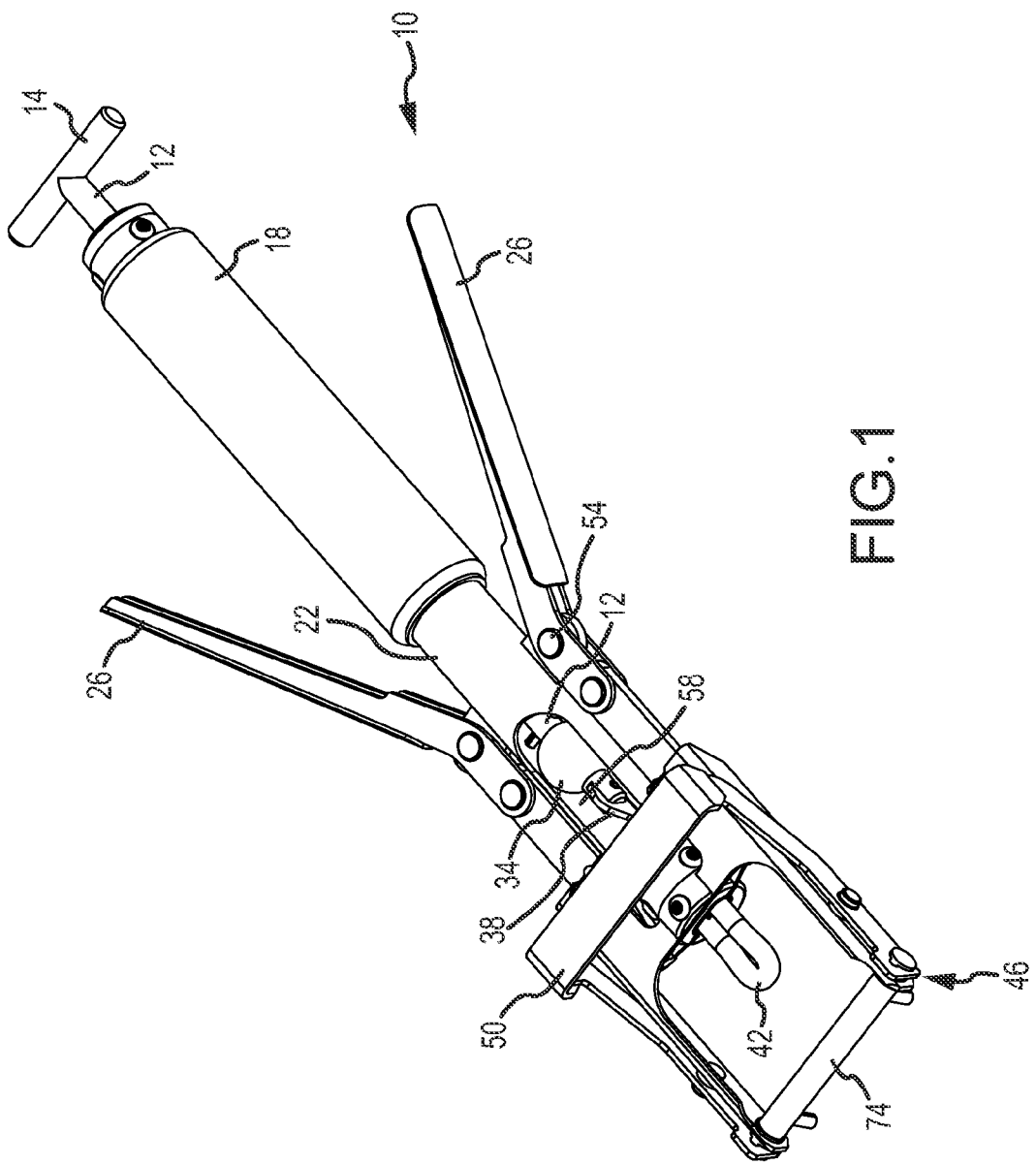
FIG. 1 is a perspective view of one embodiment of the present invention.

Referring now to FIG. 1, a ligation device 10 according to one embodiment is shown. The device 10 may comprise a tightening rod 12 and corresponding grip or handle 14 for applying tension to a loop or band 42 at a distal end of the device 10. A tightening rod may extend coaxially through a main portion 22, which extends longitudinally between a handle 14 and a band 42. The tightening rod 12 and/or main portion 22 may be comprised of various materials known to those of skill in the art. For example, a tightening rod 12 and/or main portion 22 may be comprised of a stainless steel, titanium, or various other materials which provide sufficient durability and resistance to stress and corrosion.

At least a portion of a length of a main portion 22 may be wrapped or coated with a grip 18. Grip portions 18 of the present invention may be comprised of a variety of materials known in the art such as rubber or foam sleeves, including, but not limited to, cork tapes, NPVC (or Nitrile) foam tubing, neoprene, silicone, EPDM foam, and various other materials known in the art. It will be recognized that an objective of a grip portion 18 as provided in the present invention is to allow a user to comfortably grasp the device 10. Accordingly, one of skill in the art will recognize various materials and devices through which this may be accomplished. In an alternative embodiment, a grip portion 18 may be comprised of recesses in the main body portion 22 which accommodate digits of a human hand, thus providing a comfortable grip and reducing the risk of slippage or dropping of the device 10. In yet another embodiment, an extension off of the longitudinally extending main portion 22 is provided which allows a user to grip the device 10 and apply tension to a band 42 via the tightening rod 12. For example, a handle or extension may be provided at an angle between 60 and 120 degrees from a centerline of a tightening rod 12. In a more preferred embodiment, this extension may extend from a main portion 22 at an angle between 75 and 105 degrees from a centerline of a tightening rod 12.

A main portion 22 may be comprised of a substantially hollow member with an aperture 58 or access point provided to allow for user access to various components disposed within the main portion 22. According to various embodiments of the present invention, a band 42 and attached hook or tang (62 in FIG. 2) is applied to an animal and subsequently deployed from additional aspects of the present invention. Accordingly, for subsequent ligation procedures, it is necessary to reapply a band 42 to various components of the invention 10. This may be accomplished by the aperture 58 formed through a side wall of a main portion 22 which allows for the attachment of a hook 38 to a ligature band 42. The aperture 58 may serve various additional functions, such as providing access for servicing, repair, and/or cleaning of interior regions of the present invention.

In one embodiment, a coaxial relationship between a tightening rod 12 and a main portion 22 is established and maintained by a centering device 34. The centering device 34 may be comprised of, for example, a substantially spherical object which occupies a substantial portion of an interior diameter and/or circumference of a main portion 22. This device 34 may further be comprised of various known materials such as various metals, PVC, HDPE, LDPE, ceramics, and similar materials which may provide a sufficiently low coefficient of friction between the centering device 34 and an interior surface of the main portion 22.

Those of skill in the art will recognize various other devices which may be employed to establish and maintain a generally coaxial relationship between a tightening rod 12 and a surrounding portion 22. For example, the tightening rod 12 may be designed to pass through various eyelets or guides within a generally tight tolerance. It will also be recognized that where maintaining such a coaxial relationship is not necessary or desirable, a centering device 34 need not be employed. The present invention therefore contemplates a tool which does not rely on such a feature. However, as it is generally desirable to apply tension to a band 42 by applying force in a substantially parallel manner, a preferred embodiment contemplates the use of such a centering device 34.

Once the desired amount of tension is applied to a body part, a clamp or adjustable device (66 in FIG. 2) may be secured around a portion of a band 42 in order to secure the tension and deploy the band 42. Therefore, in order to crimp a band 42, hinged levers 26 may be provided. Hinged levers 26 may be comprised of a variety of materials, such as those used for the main portion 22 of the device 10 as previously discussed, or a variety of other materials known to withstand forces, including abrasion, moment, and corrosion. Hinged levers 26 may include multiple linkages which allow for forces applied by a user to be translated to a ligation loop 42 portion 66 to be crimped. Linkages may be connected by a variety of hinges 54 which allow for the force and movement applied to hinged lever 26 to be translated and imparted upon a distal portion of the device 10. Accordingly, as shown in FIG. 1, when hinged levers 26 are compressed toward a main portion 22 of the device 10, hinges 54 and linkages may allow for the same or similar inward movement of a portion of the devices that causes crimping upon at least a portion of a loop 42 disposed within a distal end of the device 10. It will be recognized that where work area or user size is limited, crimping may be accomplished by providing a single lever arm which may crimp a crimping band 66.

Those of skill in the art will recognize a variety of additional means by which crimping may be accomplished. For example, devices may be provided to assist those of smaller stature or strength. In one embodiment, the present invention contemplates the use of various cranks and pull-triggers which may provide a user the ability to more gradually contract hinged members 26 or similar crimping devices. In an alternative embodiment, the present invention may additionally comprise a servo-motor or similar device capable of crimping a ligation band 42 by simply pushing a button and actuating the motor or similar device. Certain embodiments of the present invention include on-board power supplies, such as batteries, or may be capable of receiving power from an external source, such as an AC outlet, in order to assist in crimping procedures. The present invention also contemplates the use of various means of stored energy, such as pneumatic pressure which may be released as a single pulse, to crimp or secure a ligature band 42. Various devices known in the art, such as staple guns and nail guns, provide the ability to impart a pulse which may be suitable for crimping procedures in accordance with the present invention.

Those of skill in the art will recognize that it may be difficult, time consuming, or dangerous to apply a band 42 to a body part. Particularly when, for example, a band 42 is to be positioned around a bull's or calf's scrotum, it is desirable to place the band 42 in its desired position as quickly and accurately as possible. Thus, in one embodiment of the present invention, a pre-tensioning device 46 may be disposed on a portion of a ligation device 10. The pre-tensioning device 46 may be provided as an optional attachment or as an integral portion of the device 10. As will be described in more detail herein, the pre-tensioning device 46 may provide the ability to position an expanded or tensioned band 42 around a scrotum or body part to be ligated and allow for the subsequent removal of tension by simple manual operation. In one embodiment, removal of tension from a band 42 is conducted in a manner so as to obviate the need to use more than one hand.

Figure 3:
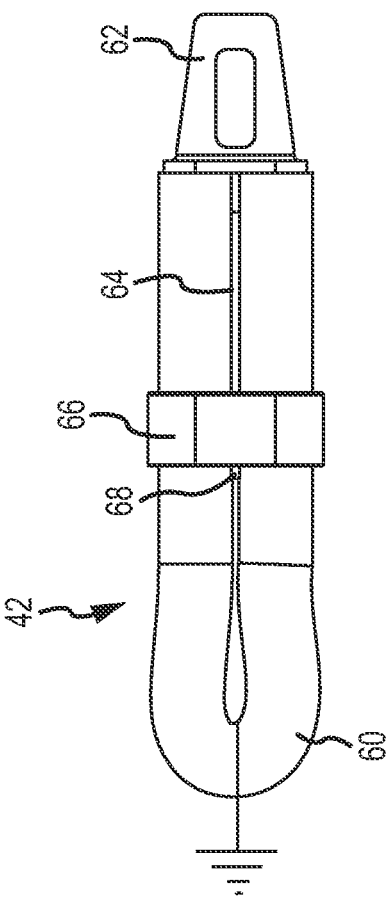
FIG. 3 is a top view of a ligation band according to one embodiment of the present invention.
Figure 2:
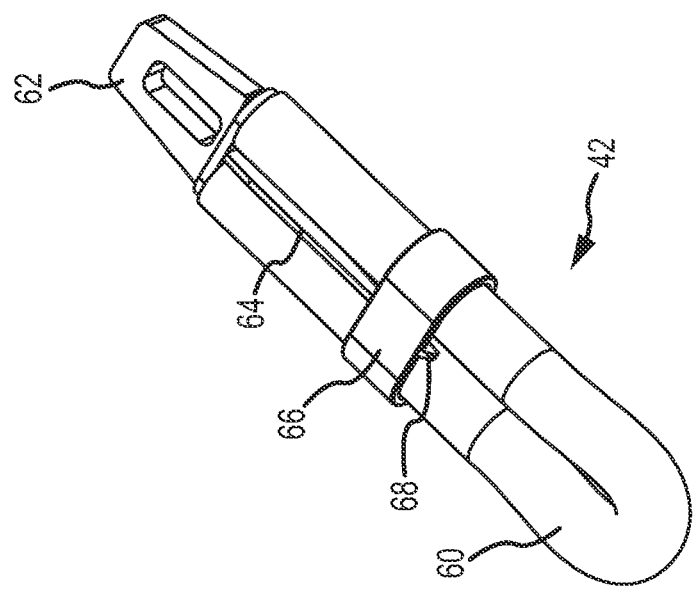
FIG. 2 is a perspective view of a ligation band according to one embodiment of the present invention.

Referring now to FIGS. 2-3, detailed views of a band 42 are shown which may be used in various ligation procedures. A loop portion 60 of a band 42 may be provided in addition to an adjustable portion 66 capable of securing a desired amount of tension, and an anchor hook 62 or tang member in fixed communication with and capable of assisting in the application of tension to the loop 60. An anchor hook or tang 62 may additionally serve to maintain a folded or closed loop position of the band 42. A loop portion 60 may be constructed from natural rubber, latex or other elastomeric material suitable for ligature procedures.

In one embodiment, a band 42 is provided wherein the loop portion 60 is preformed, secured with an anchor hook 62, and further provided with an adjustable portion 66. Preformed bands 42 of the present invention provide the ability to quickly load a band 42 into band application devices as discussed herein and simplify ligation procedures. An anchor hook 62, tang, or similar device may be secured to a ligature loop 60 in a variety of ways, including adhesive bonding, crimping, and other similar known methods and devices.

An adjustable portion or crimping band 66 may be provided which surrounds a band 42 and, when in a relaxed or un-crimped state, does not significantly inhibit longitudinal movement of a band 42 with respect to the adjustable portion 66. Accordingly, tension may be applied to a body part (not shown) by placing a loop portion of a band 42 around the body part and applying tension such that the band 42 translates through the clamp until a sufficiently small circumference of the band 42 surrounds the body part. Once the desired level of tension is achieved, the crimping band 66 may then be crimped to prevent the release of tension and other unwanted movement of the band 42. Devices and methods for crimping an adjustable portion 66 and/or band 42 will be described in more detail in further portions of this Detailed Description.

In one embodiment, the crimping band 66 comprises a specific shape, including a plurality of planar faces which are adapted to be received and/or mate with a similarly shaped portion of a ligature tool 10. Such features prohibit the undesired movement/rotation of a crimping band 66 and associated ligature band 42 during ligation procedures. Moreover, crimping bands 66 of specific sizes and shapes may correspond to a specific animal on which they are to be used. For example, as it is known that an adult bull and a young bull will require different levels of tension (and thus different bands) for ligation, a band 42 for use on a specific animal has, in one embodiment, a crimping band 66 that is only operable with a tool that provides for the proper amount of tension for that specific animal. This embodiment helps prevent the application of an improper band (i.e. one with excessive or inadequate tension). Furthermore, this embodiment helps to ensure that a crimping band 66 is properly oriented before applying compression and crimping.

In one embodiment, a hook, tang or closed loop 62 is anchored to at least a portion of the band 42. As will be discussed, an anchor hook or tang 62 may comprise one more longitudinally extending anchor members which extend into a portion of the loop 60 to provide a sufficient level of attachment and withstand tension forces which are applied during ligation procedures. The anchor hook 62 may be comprised of, for example, various nylon, plastics, or combinations thereof. Extending members of an anchor hook 62 may further include ridges, protrusions, hooks, or barbs which provide for and assist in maintaining fixed communication between an anchor hook 62 and the loop 60.

In one embodiment, ligation bands 42 of the present invention further comprise one or more extending members 64 with a hook 68 disposed at its distal end. Extending member(s) 64 and associated hook(s) 68 operate to secure a crimping band 66 in a first position (i.e. an un-crimped state). In one embodiment, extending members 64 are comprised of a plastic or similar flexible/elastic material. In a first state, crimping bands are secured by a hook 68 disposed at a distal end of at least one extending member 64. Thus, when the crimping band 66 is in an un-crimped state, the hook 68 prevents the undesired movement of the crimping band 66 toward the distal (i.e. loop) end of the band 66 due to the contact between a peripheral edge of the band 66 and a portion of the hook 68. When a crimping band 66 is to be translated toward the distal end of the loop 60 (i.e. during ligation procedures), the extending member(s) 64 and hook 68 may be easily displaced by manual force to enable freedom of movement of the crimping band 66.

Figure 4:
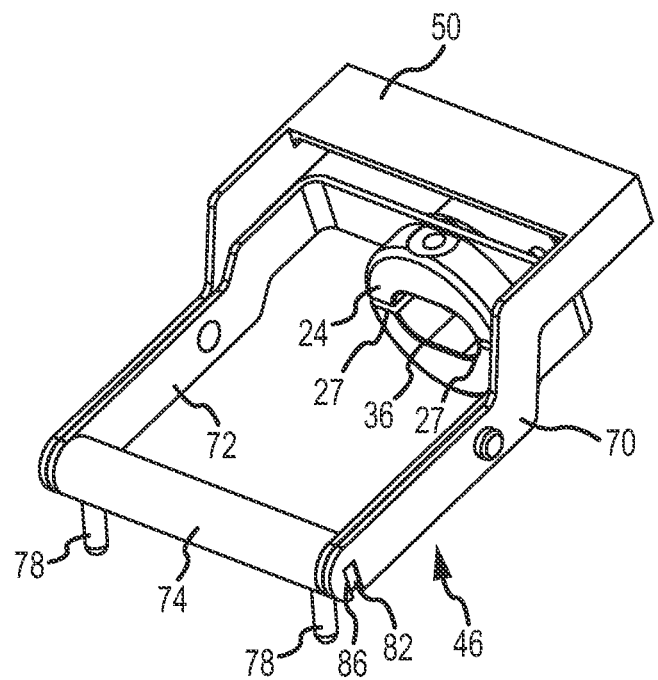
FIG. 4 is a perspective view of a pre-tensioning device according to one embodiment of the present invention.
Figure 5:
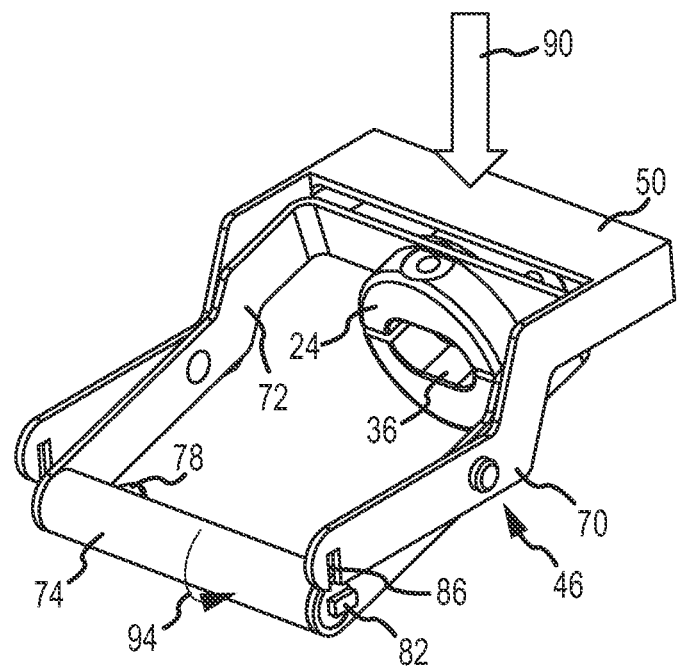
FIG. 5 is a perspective view of the pre-tensioning device shown with respect to a force being applied.

Referring now to FIGS. 4-5, a pre-tensioning device 46 is shown and described in more detail. Those of skill in the art will recognize that it may be difficult for an individual to simultaneously control or operate a ligation band, a ligation band application device, and a body part of a live animal to be ligated (e.g. a scrotum). Accordingly, the present invention contemplates a device 46 which may allow for the pre-tensioning of band 42 and subsequent quick release of the same.

In one embodiment, a pre-tensioning device 46 may be disposed on a distal end 24 of a ligation device. The device 46 may comprise an enclosure member 72 which acts to isolate and surround a part to be ligated, a rotating member 74 with extensions 78 suitable for accommodating a band 42, a hinged release member 70, and quick-release thumb plate 50. In one embodiment, as shown in FIG. 4, a rotating member 74 may be secured in a pre-tensioning position (i.e. with extensions 78 oriented generally perpendicular to a longitudinal axis of a device 10) due, in part, to members 82 which communicate and are fixed within notched members 86 of a hinged member 70. In this pre-tensioning position, a band 42 which is partially disposed within a terminal end 24 of a ligation device, may be stretched or pre-tensioned around extensions 78. The torque applied by a band 42 to the rotating member 74 may be resisted by notched members 86 and members 82. Accordingly, undesired rotation of rotating member 74 may be resisted and the band may remain in an extended or open position. It will be recognized that in this state, notched portions 82 of a hinged member in communication with members 82 of the rotating member 74 provide the required resistance to maintain a band 42 in a pre-tensioned position.

Once a pre-tensioned band is placed in a desired position (e.g. surrounding a body part to be ligated), components of the present invention allow for the simple release of tension. As shown in FIG. 5, a pre-tensioned loop may be released by applying a force 90 upon a portion 50 of a hinged member 70. As shown, a portion of a hinged member 70 may be comprised of a thumb plate 50 or similar structure which is adapted for relative ease of interaction with a human. As force 90 is applied to a hinged member 70, the hinged member 70 will rotate and previously discussed notched portions 86 will similarly rotate free of members 82 of a rotating member 74. This will allow the tension of a pre-tensioned band 42 to rotate the rotating member 74 and associated extensions 78 to the point where the pre-tensioned band 42 becomes free of the device 46 and returns to an un-tensioned state, preferably around a part which is to be ligated. Those of skill in the art will recognize that a rotating member 74 as described herein may be a freely rotating member subject to forces applied by a band 42 and/or resistance forces applied by notched portions 82 of a hinged member 70. In an alternative embodiment, a rotating member 74 may be spring-loaded and/or rotationally biased to assist in the freeing of a pre-tensioned band when a hinged member is activated and a band is released as described herein.

In one embodiment, a pre-tensioning member 46 is constructed as an integral portion of a remainder of a ligation device 10. In an alternative embodiment, a pre-tensioning member 46 comprises an optional attachment which is temporarily secured to a distal end of a ligation device 10.

As shown in FIGS. 4-5, a receiving portion 36 for a crimping band 66 is provided at a distal end of a ligation tool 10. In one embodiment, the receiving portion 36 is formed to receive a similarly shaped crimping band 66 as previously discussed. The receiving portion 36 further comprises recesses 27 which enable the crimping of a crimping band 66 via features as discussed herein. It will be recognized that although the receiving portion 36 is displayed as being disposed with its elongate axis in a horizontal position, receiving portion 36 may be oriented or rotated in any number of arrangements (particularly in a vertical arrangement).

Figure 6:
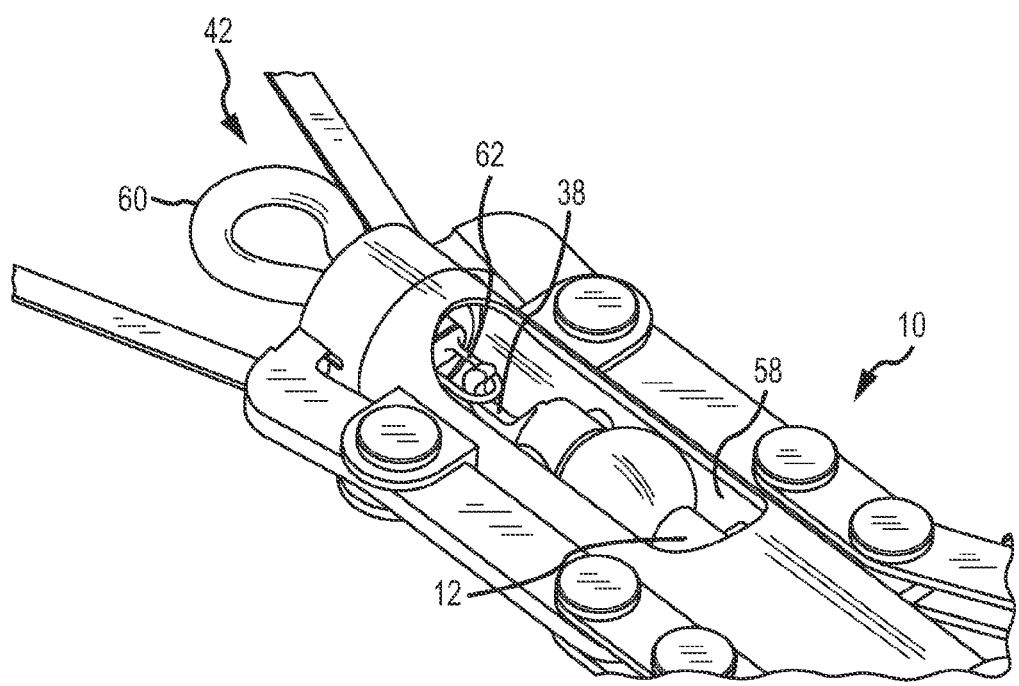
FIG. 6 is a detailed perspective view of one embodiment of the present invention.

Referring now to FIG. 6, a detailed view of a portion of a ligation tool 10 is shown. One end of a ligation tool 10 is shown with a loop portion 60 of a band 42 extending through a distal end and connected to a hook 38 of a tightening rod 12 via an anchor hook 62. An aperture 58 or cut-away is provided for visual and physical access to an interior portion of the device 10. In one embodiment, a band 42 as described herein may be loaded into the present device by placing the band 42 into a distal end of the device, with the anchor hook 62 being loaded first. Once inserted, an anchor hook 62 may be manually guided to interface with a hook 38 disposed on a tightening rod 12. Those of skill in the art will recognize that hook 38 may be comprised of a hook or any similar device capable of engaging and transmitting tension to a portion of a ligation band 42.

Subsequently, according to various devices and methods as described herein, a band 42 may be disposed around a body part to be ligated and the tightening rod 12 utilized to apply tension. In one embodiment, the adjustable portion 66 interfaces with one or more portions of the ligation device 10 and remains in a fixed position relative to the device. Accordingly, the loop portion 60 of a band 42 is allowed to translate through both an adjustable portion 66 and a portion of the ligation tool until a sufficient amount of tension is applied to a body part.

Once appropriate tension has been applied, hinged members 26 may be activated to apply a force to the adjustable portion 66 and secure the desired tension. Once an adjustable portion 66 is appropriately crimped, tension may be released from the non-ligating portion of the band 42 (i.e. the portion proximal to a user) by restoring the tightening rod to an un-tensioned position. Once tension is released from the non-ligating portion of the band 42, the anchor 62 may be disengaged from the hooked portion 38 of a tightening rod and the ligation tool 10 may be withdrawn from the work area. Thus, the band assembly 42 may be allowed to remain on the body part. Accordingly, there is no need to cut, adjust, or otherwise perform maintenance on a band 42 once tension has been applied. The band 42 may be allowed to remain on the animal until the ligated body part and band 42 drop away from the animal.

In one embodiment, this engaging mechanism comprises an electromagnet that communicates with a magnetic portion of the ligature band 42 and is further releasable via the interruption of a current to the electromagnet. In an alternative embodiment, the hook 38 is formed to fit securely within a portion of the ligature band 42. Hooks 38 of the present invention may be easily manipulated and/or rotated (e.g. through the use of a pushbutton) to readily engage or release a portion of a ligature band 42 as described herein.

Figure 7:
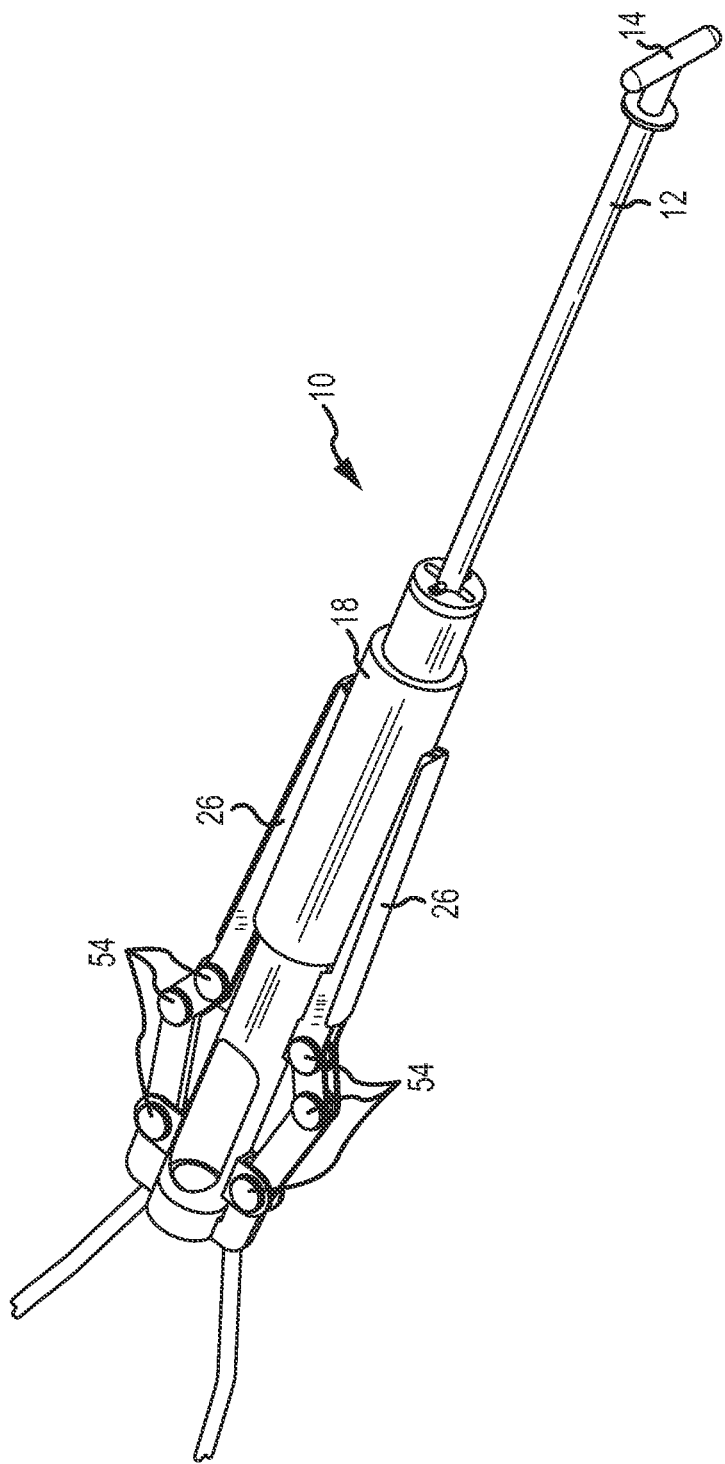
FIG. 7 is a perspective view of one embodiment of the present invention.

FIG. 7 is a perspective view further illustrative of articulating hinged members 26 useful for crimping a band 42. Hinged members 26 are shown in a closed or "crimped" position, wherein hinged members 26 have been activated to apply a crimp to an adjustable portion 66 of a band 42. One advantage of the present invention is the ability to apply a crimping force to the sides of an adjustable portion 66. It is known that complications may arise where improper or inadequate crimping occurs. For example, known crimping devices and methods may leave a gap between ends of a loop 60 or similarly may result in an overhang or protrusion of a metal clip into a ligation area or circumference. These results can lead to infliction of pain and/or harm to an animal and unsuccessful ligation. Accordingly, it is desirable to provide a device and method that allows for a ligation band 42 to be placed around a body part wherein the inner circumference of a crimped band 42 is comprised solely of rubber, latex, or similar ligation band material. In other words, once a band 42 is crimped and allowed to remain on an animal, the animal part should interface exclusively with a loop portion 60. By applying lateral forces through hinged members 26 and hinges 54, the present invention allows for a side crimp. This side crimp helps to ensure that gaps in the loop 60 do not remain and that portions of an adjustable portion 66 will not contact a part to be ligated.

In one embodiment, lateral crimping is accomplished through the use of at least two articulating levers which may be actuated at a distance away from the crimp site. Three pivot points per lever/side may be provided to translate the application of an inward force applied to levers to a crimping band 66.

Figure 8:
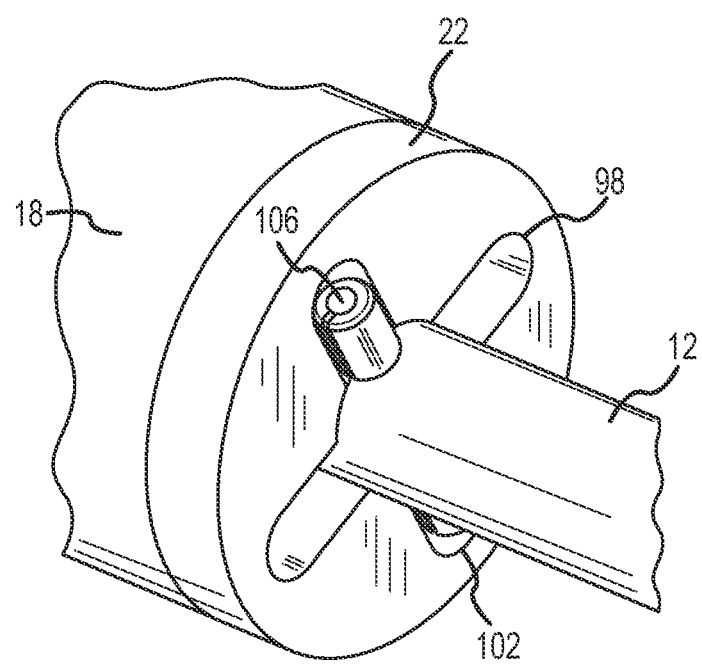
FIG. 8 is a detailed perspective view of one embodiment of the present invention.

FIG. 8 is a perspective view of one embodiment of the present invention. As previously described, it may be desirable to limit the amount of discretion as to tension applied provided to a user of a ligation device, due to the fact that excessive or inadequate tension may frustrate ligation efforts or cause them to fail. In order to provide guidance as to proper tension to be applied, as well as to help secure tension, one or more extensions 106 may be provided along a length of a tightening rod 12. Extensions 106 may be disposed within and allowed to travel through troughs 98 of a main portion 22 as tension is applied and/or released (i.e. the rod is translated). Once tension has been applied and a user desires to secure that amount of tension, a tightening rod 12 may be rotated so that extensions 106 are allowed to come to rest in grooved or notched regions 102 of a proximal end of a main portion 22.

In an alternative embodiment, a series of extensions 106 may be provided along a length of a tightening rod 12. Different extensions 106 may, for example, correspond to different levels of tension applied (e.g. for different sized animals, body parts, and/or bands to be applied). These extensions 106 may be calibrated and spaced apart so that they correspond to specific levels of tension. Different extensions 106 may be color coded so that they correspond to different tension levels and/or correspond to different ligation bands of the present invention which may be similarly color coded. Alternatively, extensions 106 are provided at various increments, which allow a user a certain limited level of discretion as the level of tension to be applied.

In an alternative embodiment, visual indicators are be provided along a length of a tightening rod 12 to inform a user as to an appropriate, inadequate, and/or excessive amount of tension being applied. Additional devices, such as stop pins may be provided to secure the tightening rod 12 in a desired position. In an alternative embodiment, spring loaded pins extend from an interior portion of a tightening rod 12 once appropriate displacement is reached. Spring loaded pins indicate a desired level of extension/tension and provide securing means that prevent a tightening rod from retracting back toward and un-tensioned state.

In alternative embodiments, tension sensing means, such as strain gauges and similar equipment may be implemented to evaluate tension applied. Tension sensing means may further be connected to signal processing means and display to a user when appropriate tension has been achieved or exceeded. In one embodiment, tension indicators as described in U.S. Pat. No. 6,409,738 to Callicrate are incorporated into features of the present invention.

Figure 9:
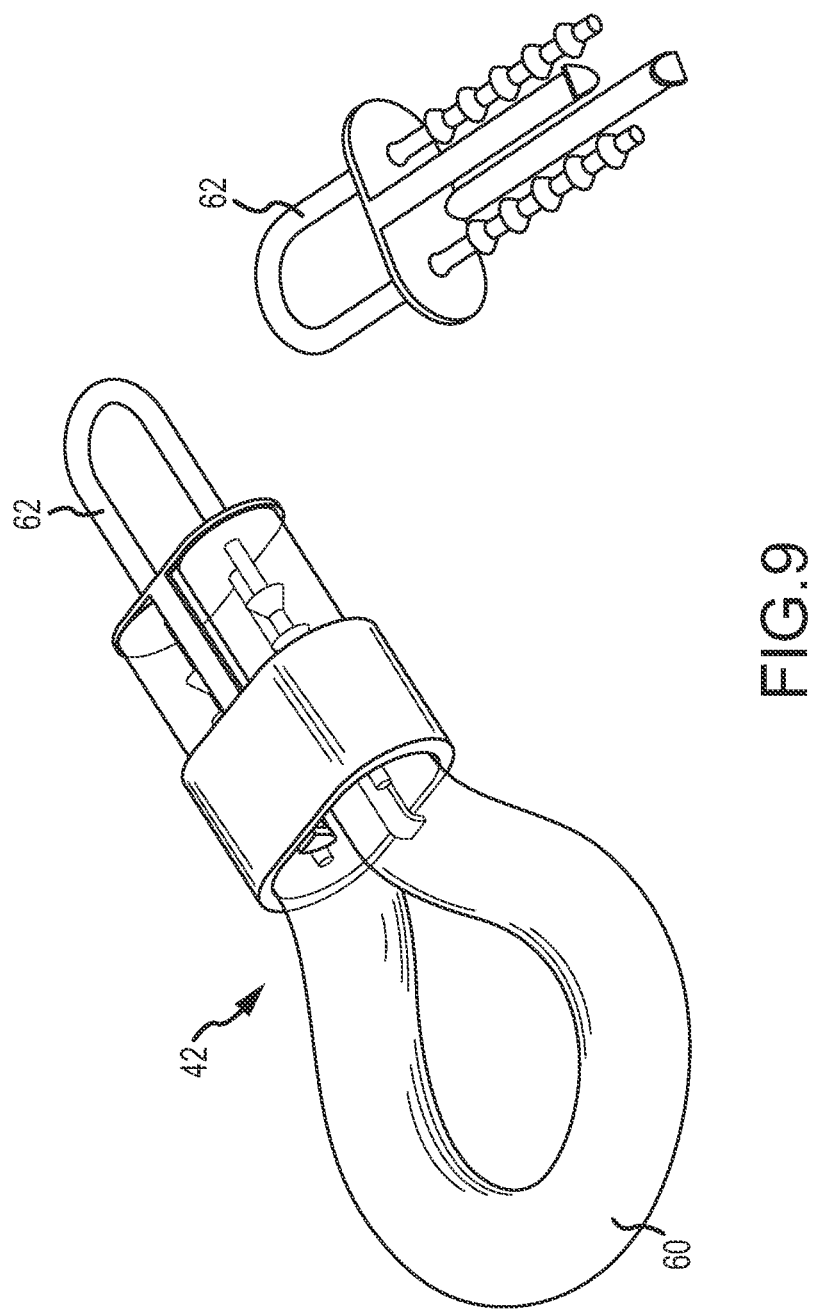
FIG. 9 is a detailed perspective view of a loop according to one embodiment of the present invention.

FIG. 9 is a perspective view of various components of a band 42 according to one embodiment of the present invention. In addition to a fully assembled band 42, an anchor hook portion 62 is shown in isolation. Anchor hooks 62 of the present invention may comprise extensions disposed within a portion of a loop 60 to help secure an anchor hook 62 and a loop 60 in fixed communication with each other.

Figure 10:
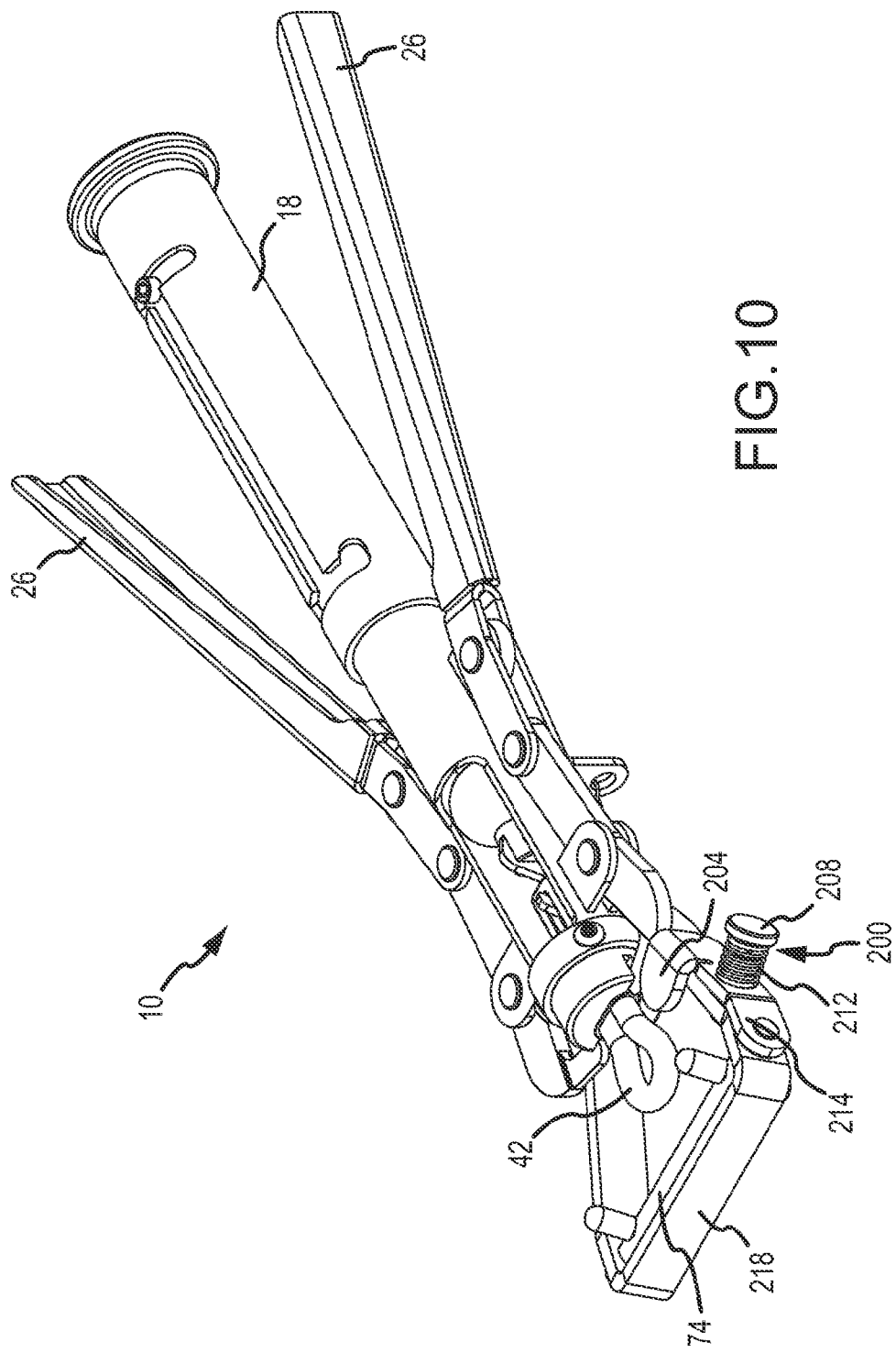
FIG. 10 is a front perspective view of one embodiment of a ligation band application tool of the present invention.

FIG. 10 is a perspective view of a ligation tool according to one embodiment. Such embodiments comprise a release mechanism 200 which facilitates or enables the release of a ligature band 42 with minimal user input. For example, such embodiments may include a stop pin 208 for preventing rotation of a rotating member 74 and maintaining a ligature band 42 in an elongated or tensioned state. The stop pin 208 is outwardly biased from a portion of the device by at least one biasing member, such as a spring 212. In certain embodiments, a rotating member 74 as shown and described herein may be restrained or mobilized by an attachment portion 214 extending around a periphery of the device and comprising a translatable stop pin 208 and a receiving member for said stop pin on a non-rotatable portion 218 of the device.

In certain embodiments, a stop pin 204 comprises an extending portion, such as a head or flange which prevents translation of the pin 204 in a first position despite a biasing force being applied by a spring 212 or similar biasing member. In certain embodiments, the invention further comprises a trigger portion or thumb plate 204 for depressing a portion of the device in a manner that allows for the head of the stop pin 208 to align with a through hole in a non-rotatable portion 218 of the device. Once alignment is achieved, the spring 212 may translate the pin to a position where the pin is no longer capable of preventing rotation of a rotatable part of the device. Thus, in certain embodiments, an expanded and/or tensioned ligature band may be released from a rotating member 74 by applying a downward force achievable by a human thumb or finger. Accordingly, various embodiments of the present invention facilitate rapid, accurate, reproducible, and/or reliable placement of a ligature band around a body part to be ligated.

Figure 11:
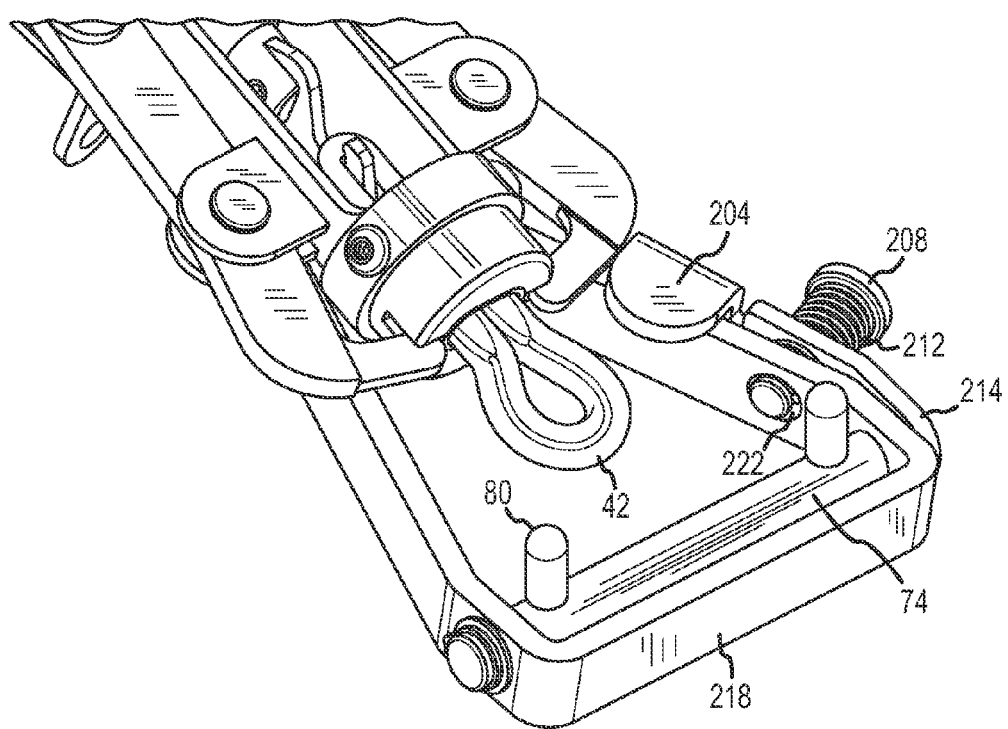
FIG. 11 is a perspective view of a ligation band application tool according to one embodiment of the present invention.

FIG. 11 is a perspective view of one embodiment further illustrating a pin 208, biasing member 212, rigid portion 218 with a through hole 222, a rotatable member 74 for maintaining a ligature band 42 in an extended position, and a user interface 204. In certain embodiments, a rotatable member 74 is connected to a rigid portion 214 comprising a thumb plate or user interface 204. A rotating member 74 is secured in a first position such that it may resist a torque applied to it through extensions (not shown, but 78 in FIG. 18) and an attached band 42. A torque is at least partially resisted in a first state by a rigid extension 214 and corresponding pin 208. As will be recognized by one of ordinary skill in the art, a torque applied to a rotating member 74 is translated to a rigid member 214 which applies a moment upon a pin 208. The pin experiences a shear force due to the moment applied by the rigid member 214 and contact with a bracket or rigid portion 218 of the tool. In various embodiments, the shear force and material properties of the pin 208 provide the necessary resistance for preventing rotation and maintaining a ligature band 42 in an extended or tensioned position facilitating placement of a band around a body part.

In various embodiments, a biasing element 212 is provided. As used herein, a biasing element refers to both linearly and non-linearly biased devices. In one embodiment, a pin comprises a spring pin, such as McMaster-Carr Part No. 98195A015 and a biasing element 212 comprises a coil spring such as McMaster-Carr Part No. 9435K52. The present invention is not limited to any particular device, feature, dimension, product, or other detail. Rather, various references to part numbers, dimensions, and features are provided herein merely to provide additional support and further enable the present disclosure.

One of skill in the art will recognize that it is often desirable in ligature procedures to minimize the amount of user manipulation and/or time required to place a band around a particular body part. Accordingly, release mechanisms as shown and described herein increase the simplicity and reduce safety risks in ligature procedures with respect to human users and animal subjects alike. As shown in FIG. 11, a ligation device is provided with a ligature band 42. Although shown in an un-tensioned state, the band 42 may be stretched and placed around members 80 to position a band 42 in a stretched/tensioned state. The force imparted upon a rotating member 74 by a band is resisted and rotation is prevented by a lever 214 and translatable pin 208. In certain embodiments, the pin 208 is provided with a flange or head which contacts a rigid portion 218 of the device and prevents a spring 212 from translating the pin in an outward direction in a first position. Thus, in certain embodiments, a spring 208 is provided which, in a first position, is adapted to resist at least a shear force applied by band 42 and lever 214 combination as well as resist translation due an axial spring force.

In various embodiments, a user-interface portion 204 is provided. A user-interface portion 204 or a thumb plate provides a generally planar surface adapted for human contact. The generally planar surface portion is adapted for receiving and transmitting a user-applied force. For example, a downward force applied by a human thumb can depress the plate toward a portion of the device (e.g. 218), thereby counteracting the force applied to a rotating member 74 and lever 214 by a band 42. Upon the application of an appropriate amount of force, the lever will be displaced to a position wherein the pin 208 and flange portion of the pin 208 is generally aligned with a through hole 222. Upon achieving proper alignment, the spring 212 will act to eject a pin 208 from a through hole 222. Thus, various embodiments of the present invention comprise the ability to release a band and associated tension maintaining devices through, for example, one-handed or single-finger operation.

Although various figures depict a device comprising a single stop pin and spring combination, one of skill in the art will recognize that any number of rotation limiting and pin release mechanisms may be disposed on devices on the present invention. For example, a similar or identical feature may be disposed opposite the pin and spring combination shown in FIGS. 10-11.

It will further be recognized that thumb plates and/or release mechanisms of the present invention may be disposed at any number of locations on the device. For example, a thumb plate may be located at either a distal or proximal end or at any number of locations therebetween. In various embodiments, the thumb plate is disposed at a proximal end of a device and connected to a distal end of the device through a rigid connecting member and/or lever. In alternative embodiments, a thumb plate or release mechanism is disposed on one or more hinged members 26 adapted for crimping a band.

Figure 12:
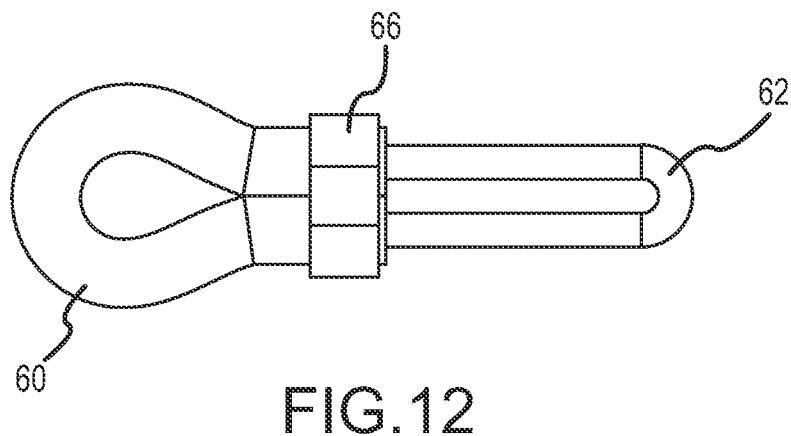
FIG. 12 is a top plan view of a ligation band according to one embodiment of the present invention.
Figure 13:
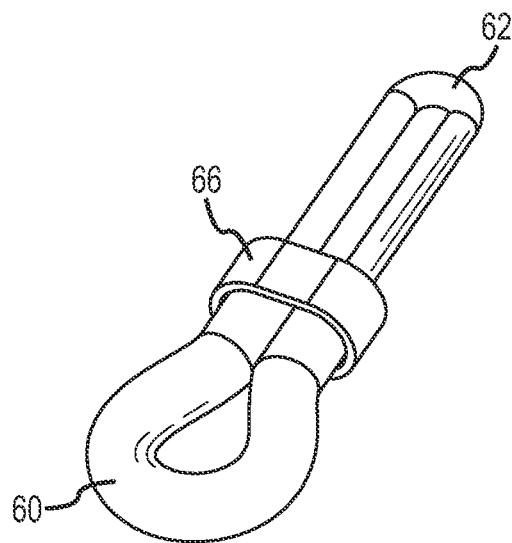
FIG. 13 is a front perspective view of a ligation band according to one embodiment of the present invention.

As shown in FIGS. 12-13, a ligature band of a predetermined length is provided. In certain embodiments, a ligature band is provided that is comprised of an elastomeric material of a predetermined length which is folded and/or shaped to form a closed loop 60. Two ends of the predetermined length of the elastomeric material are disposed substantially parallel to each other and an anchor member 62 or tang portion is secured to the two ends of the elastomeric material of predetermined length. In certain embodiments, a crimping band 66 is provided, the crimping band being translatable along at least a portion of the length of a band in an uncrimped state.

In various embodiments, a closed loop 60 may comprise a natural latex rubber and various other similar materials having elastomeric properties. Anchor members may be comprised of any number of materials known to generally withstand tension forces. For example, anchor members of the present invention may be comprised of any one of the group consisting of 4043 aluminum, various other aluminums, stainless steel, titanium, rigid plastics, high density polyethylene, low density polyethylene, polystyrene, nylon, rubber, synthetic rubber, PEEK, ultra-polymers, high performance polymers, mid-range polymers, and commodity polymers. In various embodiments, anchor members comprise materials which are generally resistant to corrosion and thereby provide a loop and anchor member which is generally resistant to corrosion, particularly when left to reside on the body part of an animal for various periods of time. One of skill in the art will recognize that where detachable ligation bands are applied to an animal and the animal is thereafter allowed to reside or generally be exposed to outdoor environments, it is desirable to prevent or avoid corrosion of various parts of the band which may come into contact with the animal and/or other animals. Accordingly, various embodiments of the present invention contemplate providing a band comprised at least partially of elements adapted for avoiding, preventing, or resisting corrosion.

One of ordinary skill in the art will recognize that where tension is applied to a ligature band through an anchor member, the anchor member and means of attaching the anchor member to the band must be capable of withstanding a certain degree of tension and/or force. Therefore, in various embodiments, an anchor member is secured to a ligature band using one or more adhesives and/or bonding agents. Adhesive and bonding agents suitable for use in various embodiments of the present invention include, but are not limited to anaerobic adhesives, cyanoacrylate adhesives, two-part epoxies, single-part epoxies, structural acrylics, UV light curable adhesives, polyurethane reactive adhesives, two-part urethane adhesives, acrylic adhesives, solvent or water based adhesives, contact bond adhesives, and similar substances. In one embodiment, Permabond 792 Cyanoacrylate is applied to bond anchor members to ligature bands to at least partially assist in the secure attachment of the anchor members and the bands.

Figure 14:
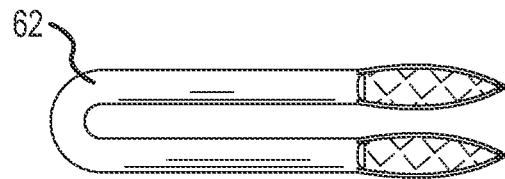
FIG. 14 is a top plan view of an anchor member according to one embodiment of the present invention.
Figure 15:
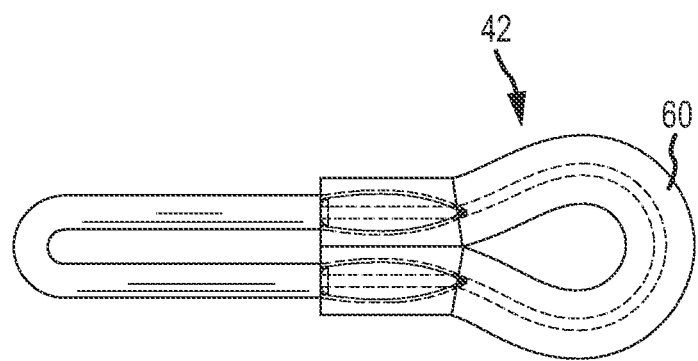
FIG. 15 is a top plan view of an anchor member inserted into a ligation loop according to one embodiment of the present invention.

As shown in FIGS. 14-15, an anchor member is provided. In various embodiments, an anchor member comprises a first end and a second end, the first end comprising one or more members for insertion into a band, the second comprising a U-shaped member, and two elongate members positioned therebetween. In various embodiments, members for insertion comprise geometries and/or surface features adapted for securely fixing an anchor member within an elastic member (see, e.g. FIG. 15).

In certain embodiments, portions of anchor members are preferably formed or shaped to increase surface area and generally promote secure attachment to a ligature band. In various embodiments, anchor members comprise ridges or protrusions to both increase the amount of surface area of the anchor member in contact with the ligature band as well as create portions or regions wherein a normal force is applied between the anchor member and the ligature band upon the application of tension upon a loop 42. Furthermore, in various embodiments, portions of anchor members are shaped to receive and/or maintain bonding agents and adhesives.

In various embodiments, portions of anchor members are formed and/or shaped so as to prevent, limit, and/or reduce the amount of bonding agent that is pushed or scraped off of an anchor member when the anchor member is inserted into the ligature band. One of skill in the art will recognize that where a bonding agent is initially applied to a portion of an anchor member and the anchor member is thereafter inserted or press fit into a ligature band, the ligature band is likely to scrape, remove, or otherwise dislocate a bonding agent from the anchor member. Therefore, in various embodiments, anchor members of the present invention are shaped so as to shelter adhesive agents and prevent the removal of one or more bonding agents as the anchor member is applied to the ligature band. For example, as shown in FIG. 14, ridges, rasps, recessions, dimples, scales, and/or various similar features and combinations thereof are provided on at least a first end of anchor members which are adapted to house and/or protect adhesive agents as an anchor member is securely placed within a loop.

Figure 16:
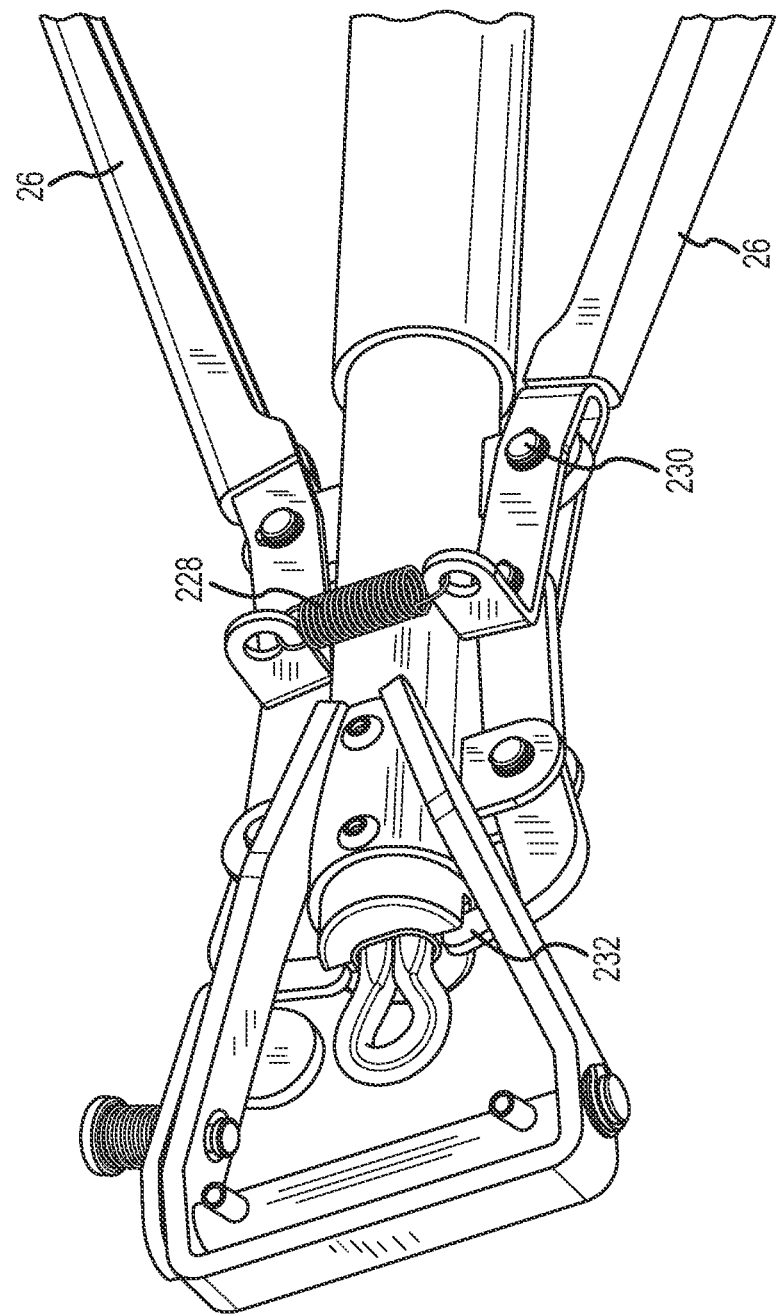
FIG. 16 is a bottom perspective view of a ligation band application tool according to one embodiment of the present invention.

FIG. 16 is a bottom perspective view of one embodiment of the present invention. As shown, a lever biasing member 228 is provided for biasing crimping arms in an outward direction. In one embodiment, a lever biasing member 228 comprises a coil spring adapted to apply a tension force on lever arms 26 via one or more hinges 230. Accordingly, in various embodiments, lever arms 26 may be directed inward under a force achievable by a human user which is sufficient to overcome a spring force provided by a lever biasing member 228. However, when no external forces are applied to a ligation tool, the lever biasing member is adapted to provide sufficient force to restore levers 26 to an initial position. In various embodiments, an initial position comprises a position wherein levers 26 as well as crimping tangs 232 are in an expanded state (i.e. with respect to one another and/or a tool/band).

Figure 17:
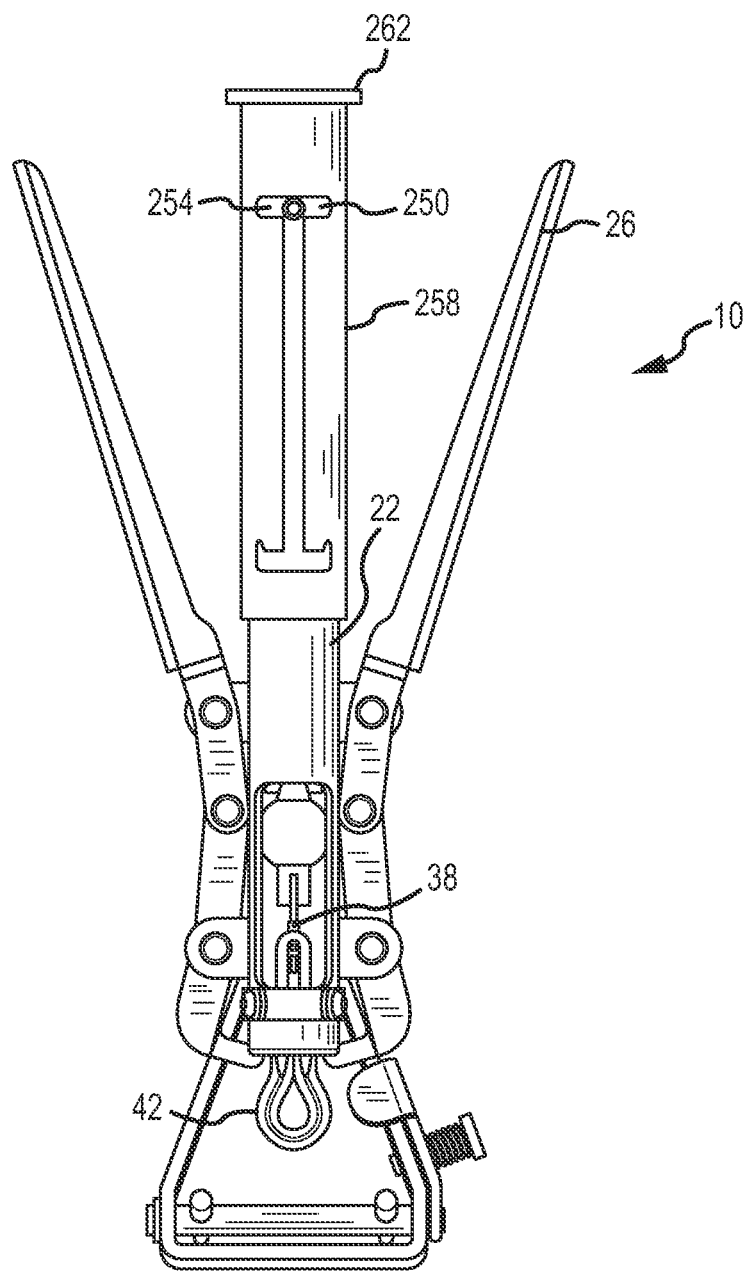
FIG. 17 is a top plan view of a ligation band application tool according to one embodiment of the present invention.

FIG. 17 is a top view of one embodiment of the present invention wherein a sleeve 258 is provided for applying tension to a band 42. In various embodiments, a sleeve 258 is provided and disposed generally concentric with a shaft portion 22 of the tool 10. The shaft portion comprises an extension 254 or protrusion adapted for securing a sleeve 258 and/or securing a rotational or translational position of the sleeve. In various embodiments, one or more slots or channels 250 are provided in a sleeve 258. One or more protrusions may be disposed within a channel 250 of the sleeve 258, the protrusion/channel combination being adapted for guiding translation and/or rotation of the sleeve 258 with respect to the shaft 22. In various embodiments, the protrusion/channel combination is adapted for selectively securing the sleeve 258 in a desired location, thereby securing the tension applied to a band 42 and allowing a user to divert attention and/or manipulation to levers 26 for crimping the band 42.

In various embodiments, a tightening rod 12 is disposed within the shaft 22 and sleeve 258 and securely connected to a proximal portion of the sleeve. The sleeve may further comprise various features to facilitate gripping, pulling, and/or rotating of the device 10 and sleeve 258 by a human hand. For example, in certain embodiments, a flange 262 is provided at a proximal end of the sleeve 258 to reduce the risk of a user's hand inadvertently becoming detached from the sleeve. In various embodiments, an outer portion of the sleeve is comprised of a rubber and/or textured surface to facilitate user manipulation of the sleeve 258.

In various embodiments, a sleeve 258 comprises various gripping and rotation assistance features. For example, gripping features of the present invention comprise protrusions and indentations adapted for receiving a user's hand and/or finger(s). In certain embodiments, the present invention comprises extensions or levers extending generally radially from a sleeve 258 adapted for creating a mechanical advantage for applying a torque to the sleeve.

In alternative embodiments, a sleeve portion 258 comprises a handle portion. For example, a generally T-shaped extension may be provided which extends from a proximal location of the sleeve 258. In such embodiments, a user may apply tension to a ligation band and/or rotate and secure the sleeve position by manipulating either one of the sleeve 258 itself or a handle portion. In various embodiments, channels 250 comprise an L or T-shaped arrangement on at least a distal end wherein laterally extending channels terminate with a longitudinal extension for maintaining a position of the sleeve. One of ordinary skill in the art will recognize that where a tension force of sufficient magnitude is applied by a band 42, the sleeve may slide out of a locked position if not properly secured. Thus, in addition to frictional forces provided between the sleeve 258 and the protrusion 254, the present invention contemplates further locking or cradling the protrusion 254 such that a normal force is applied between a portion of the sleeve 258 and pin 254 when torsion is applied to the sleeve or shaft.

In one embodiment, different sized bands 42 are provided in order to perform ligation on different sizes, types, ages, etc. of animals. Various devices known in the art employ an endless loop band. Although endless loop bands may accommodate various different size animals and parts, they may present a risk of applying excessive or inadequate tension. Various embodiments of the present invention provide for constraints that may limit the amount of discretion a user has over tension to be applied. Additionally, due to the fact that these constraints may only be appropriate for certain sized animals or body parts, the present invention further contemplates the use of different sized bands 42. For example, a band 42 is provided that is suitable for ligation of small animals, such as infant calves or sheep. A band 42 of similar design is further provided for a medium sized animal, such as a more developed calf. This medium sized band 42 is larger in initial circumference and/or has a higher elastic force. Bands 42 may also be provided for larger animals, such as grown bulls. These bands are further color coded and/or labeled so as to readily provide information to a user and reduce the risk of using an improper band and resulting failed ligation.

In accordance with various features and components of the present invention, a method of using the same will now be described. Ligation procedures may be performed by first inserting a ligation band 42 into a distal end of a ligation device 10. The ligation band 42 may then be manually expanded to extend around extensions 78 of a rotatable member 74 of a pre-tensioning device 46 in a closed position. With a ligation band 42 in a pre-tensioned position, the device 10 may be placed against an animal part (e.g. scrotum) and the part worked into the loop 42 with a free hand. Once the loop 42 is properly situated, force may be applied to a thumb-plate 50, allowing the rotatable member 74 to rotate and the pre-tensioned band 42 to return to a non-expanded state. Tension may then be applied to a tightening rod 12 via handle 14 to securely tighten the band 42 around the part. Once the desired or indicated maximum tension is reached, the handle 14 and tightening rod 12 may be rotated to a locked position or similarly secured as described herein. Once the rod 12 is locked, hinged levers 26 may be actuated to compress and crimp or secure an adjustable portion 66 of the band 42. Once the band 42 is secured by crimping or securing the adjustable portion 66, the anchor hook 62 may be freed from a hooked end 38 of the tightening rod 12. Accordingly, the band 42 is now secured to the part to be ligated and the remainder of the device 10 may be removed from the work area. The band is allowed to reside in a tensioned state around the part to be ligated until the part to the ligated and the band drop away from the animal. Thus, there is no need to cut or sever portions of ligature material and/or a ligature band.

FIG. 18 is a perspective view of a ligation device 300 according to one embodiment of the present invention. As shown, a ligation device 300 is provided wherein tension on a ligation band 314 is maintained by a locking mechanism. The locking mechanism allows linear motion in the ligation band in a tightening direction while preventing motion in an opposing direction. The ligation device 300 comprises a handle 302, a shaft 304 having a hollow interior, a tightening rod 308 disposed within the shaft 304, a hook 310, a deployable ligation band 314, an optional grip 306, and an optional pre-tensioning device 200. The handle 302 abuts the proximal end of the shaft 304 and is connected to the tightening rod 308. The handle 302 may comprise various features to facilitate gripping by a user's hand, including rubber and/or a textured surface(s). As shown, the handle 302 has a flange at its proximal end to reduce the risk of a user's hand inadvertently slipping off the handle 302. The shaft has an aperture providing visual and physical access to the interior portion of the ligation device and an end cap or receiving portion 312 with a hollow interior. The tightening rod 308 is disposed within the shaft 304 and links the handle 302 to the deployable ligation band 314 via a hook 310 connected with the tightening rod 308.

The deployable ligation band 314 comprises an elastomeric band, a collar, and a tang. The collar has an opening formed therethrough and the tang has an eyelet in its proximal end. By moving the handle away from the body part, the ligation band translates through the collar until the ligation band's circumference is sufficiently small to block off blood flow and systemic support to the body part. Once the desired tension is achieved, the handle is returned to its initial position and the hook is disconnected from the eyelet, thus allowing the deployable ligation assembly to be separated from the ligation device. A locking mechanism in the deployable ligation assembly secures the tension in the ligation band. The deployable ligation assembly remains with the animal until the body part detaches from the body.

Figure 19A:
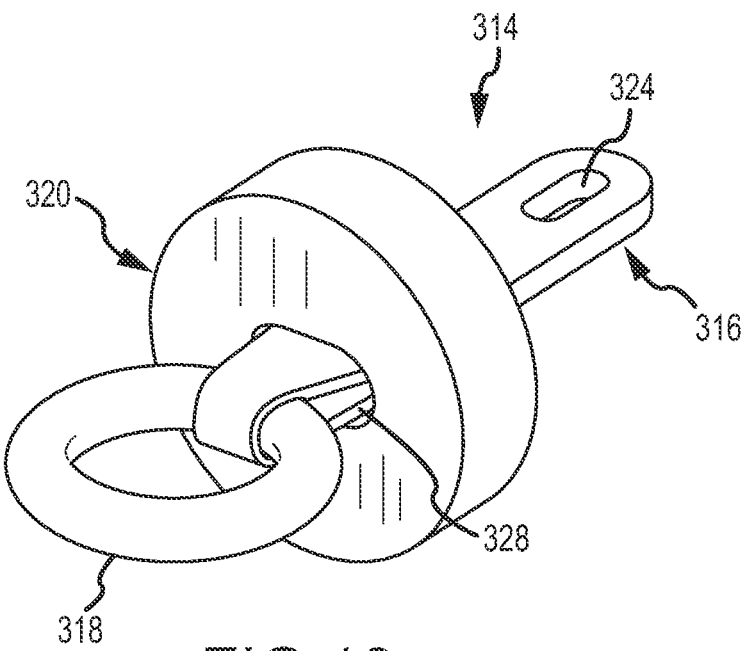
FIG. 19a is a front perspective view of a ligation band according to one embodiment of the present invention.
Figure 19B:
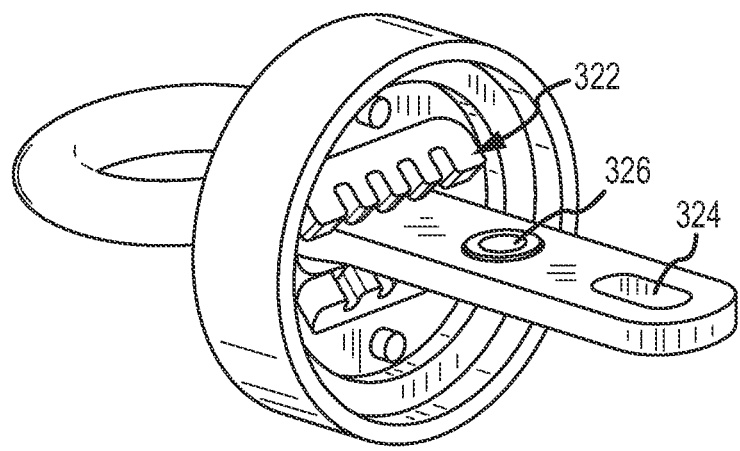
FIG. 19b is a rear perspective view of a ligation band according to one embodiment of the present invention.

Referring now to FIGS. 18, 19*a* and 19*b*, a ligation band application tool and a ligation band according to preferred embodiments are shown. FIG. 18 depicts a ligation band application device comprising a handle portion 302, a longitudinally extending shaft 304 having a grip portion 306, and a pre-tensioning device 200 disposed at a distal end of the device 300. The handle 302 is interconnected to a tightening rod 308 disposed generally within and substantially coaxial with the shaft 304. The tightening rod 308 comprises a hook 310 at a distal end for selectively and removably engaging a portion of a ligation band 314. A band receiving portion 312 is provided at a distal end of the device 300 for receiving a ligating band 314. A collar portion of a band 314, as will be further described, may be disposed within or otherwise accommodated by the receiving portion 312. The band 314 is held in a specific orientation in the receiving portion 312 and allows for the application of tension to various portions of the band 314 by an application of force to the handle 302, tightening rod 308 and hook portion 310. Communication between portions of the loop 314 and the receiving portion 312 further allow for various portions of the loop 314 to be held stationary (i.e. with respect to the device 300) while additional portions of the loop 314 are translated and/or secured.

FIGS. 19*a*-19*b* depict a ligation band according to a preferred embodiment. A ligation band 314 is provided having a pull tang portion 316 in force transmitting communication with an elastomeric loop 318 having a predetermined circumference. As one of ordinary skill in the art will recognize, the elastomeric loop 318 may be formed of a variety of elastic/elastomeric materials, including natural rubber, latex, and various materials comprising similar properties.

Additionally a retainer keeper or collar portion 320 is provided. In various embodiments, the collar portion 320 mates with a receiving portion 312 of an application device 300 and additional comprises an aperture 328 for receiving the tang portion 316 and at least a portion of the elastomeric loop 318. Preferably, the aperture 328 sized and arranged to securely engage a portion of the elastomeric loop 318 when said portion is translated through the aperture 328, such as when a force is applied by the handle 302, tightening rod 308 and hook 310.

As further shown in FIG. 19*b*, the collar portion 320 is provided with a locking means or a retainer portion 322 through which a tang 316 may be translated and which secures a portion of elastomeric material 318 that is translated therethrough. In various embodiments, locking means 322 comprises one or more angled walls to create a wedge effect and further secure an elastomeric material (i.e. allow for translation of the elastomeric portion in only one direction).

In various embodiments, locking means 322 may comprise protrusions or teeth in addition to or in lieu of angled walls to engage an elastomeric portion and allow for single-directional movement of the elastomeric portion with respect to the collar 320. As further shown in FIG. 19b, a band device 314 may comprise a tang portion having an aperture 324 for receiving or hook or similar tension-applying member. It will be expressly recognized that ligation bands of the present invention are suitable for use with any number of devices and features for translating the elastomeric portion 318 through the collar portion 320, including one or more human hands. The present invention is not limited to a ligation band device for use with any single applicator device. Indeed, it is contemplated that the novel ligation bands discussed herein may be used with any number of additional tools or, in the case of simply manual operation, without additional tools.

In various embodiments, locking means 322 comprise one or more hinged gate portions. As used herein, the term "hinged" is contemplated as generally referring to any structure that is capable of hingedly rotating with respect another portion of the device and should not be read as limiting the present invention to any particular device or arrangement of devices. Thus, in one embodiment, locking means 322 is/are hingedly coupled to the collar portion 320 and allow for rotation of locking means 322 inwardly (i.e. away from a part to be ligated by the band 318). Tension is further secured by this feature, as the locking means 322 will be disposed at an angle that will resist or prevent return of a portion of the band 318 that has been translated therethrough.

Figure 20:
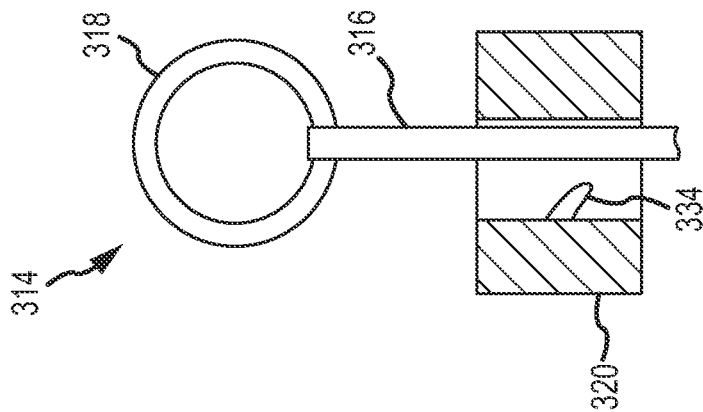
FIGS. 20-24 are additional views of alternative embodiments of a ligation band.

Referring to FIGS. 20-24, various alternative embodiments of ligation bands are provided. Referring to FIG. 20, an embodiment of a deployable ligation band 314 is shown. As shown, the deployable ligation assembly 314 comprises an elastomeric band 318, a tang 316, and a collar portion 320. The tang 316 is connected with the band 318 and is partially inserted through an opening formed in the collar 320. A plurality of teeth 330 is disposed on the tang 316 and is configured to interact with a corresponding locking mechanism 332 disposed in the collar 320 once the band 318 has contacted the collar opening. As illustrated, the locking mechanism 332 comprises a pawl disposed within the collar 320. The pawl 332 has teeth configured to engage the tang teeth 330, thus preventing withdrawal of the tang 316 from the collar 320 and securing a tension in the band 318.

In order to tighten the band 318 around a body part, a user applies tension to the tang 316 via a tensioning rod. The applied force translates the tang 316 and band 318 through the opening of the collar 320. As the tang 316 is translated through the collar opening, the convex portion of the tang teeth contact the convex portion of the pawl teeth. Upon contact, the pawl moves and allows the tang teeth to pass by the pawl teeth. Once the tang teeth pass by the pawl teeth, the pawl moves back to its initial, unstressed position. This process continues until the desired level of tension is achieved on the band 318 and the user stops applying tension to the tensioning rod. Once tension is removed from the tensioning rod, the planar portion of the pawl teeth will engage the planar portion of the tang teeth, thereby preventing retraction of the tang and securing the tension in the band 318. If the pawl 332 flexes, the back surface of the tang will contact the side wall of the collar opening, thus creating frictional forces that will prevent retraction of the tang 316. A heel may be provided on the pawl 332 to obstruct flexion of the pawl and assist in preventing linkage retraction.

It should be understood by those skilled in the art that the opening may contain additional pawls in any configuration, including stacked, side by side, or other configurations as may be desired. Additionally, the locking mechanism may comprise other forms of pivotable and flexible pawls, angled locking surfaces, or insertable barbs.

Figure 21:
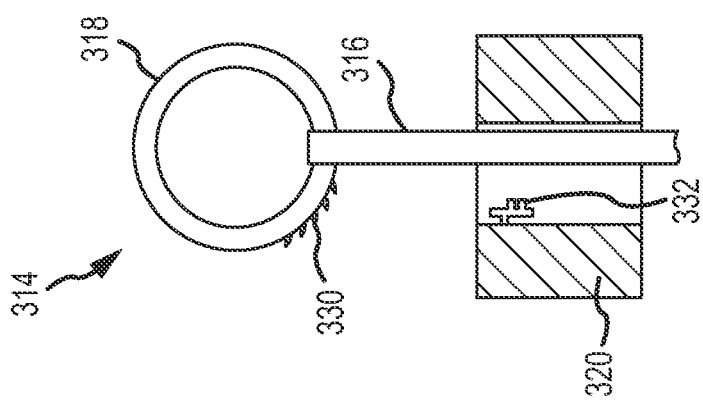

Referring to FIG. 21, another embodiment of a deployable ligation band 314 is shown. As shown, the deployable ligation band 314 comprises a elastomeric band 318, a tang 316, and a collar 330. The tang 316 is connected with the band 318 and is partially inserted through an opening formed in the collar 320. The band 318 comprises a plurality of teeth 330 and the collar 320 comprises a corresponding locking mechanism or pawl 332. The locking mechanism 332 may comprise a pawl disposed within the opening and functions in the same way as described above with regard to FIG. 20. It should be understood by those skilled in the art that the opening may contain additional pawls in any configuration, including stacked, side by side, or other configurations as may be desired. Additionally, the locking mechanism may comprise other forms of pivotable and flexible pawls, angled locking surfaces, or insertable barbs.

Figure 22:
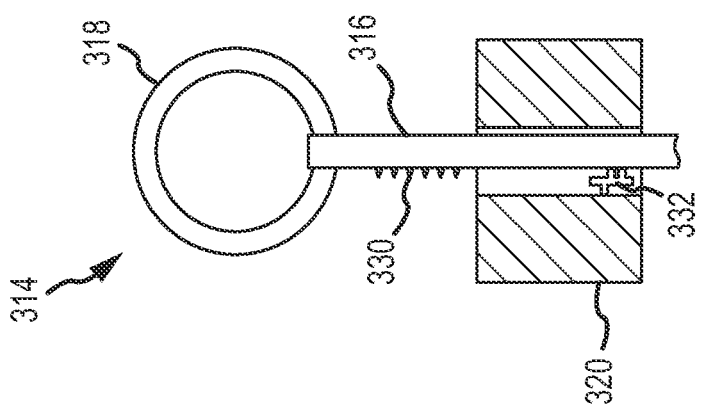

Referring to FIG. 22, a further embodiment of a deployable ligation band 314 is shown. As shown, the deployable ligation band 314 comprises a ligation band 318, a tang 316, and a collar 320. The tang 316 is connected with the band 318 and is partially inserted through an opening formed in the collar 320. A locking mechanism 334 disposed within the collar opening comprises one or more biasing members. As the band 318 is pulled into the collar opening, thereby tightening the portion of the ligation band surrounding a body part, the biasing member allow the ligation band to move through the opening. The biasing members may flex or rotate to allow this movement. However, upon opposing motion of the band 318, the biasing members 334 bear against the surface of the ligation band and produce a wedging action that binds the band 318 in the opening and prevents any further backward motion. The biasing members 334 may include ridges, protrusions, pawls, hooks, or barbs. To optimize performance, the biasing members 334 may be spring loaded to increase the binding motion of the biasing member. Additionally, high friction materials may be used to increase the friction between the biasing members and the ligation band. An advantage of this embodiment is that the ligation band and the linkage are toothless, thus reducing the cost and complexity of the deployable ligation assembly. It should be understood by those skilled in the art that the opening may contain any number of biasing members, in any configuration, including stacked, side by side, or other configurations, as may be desired.

Figure 23:
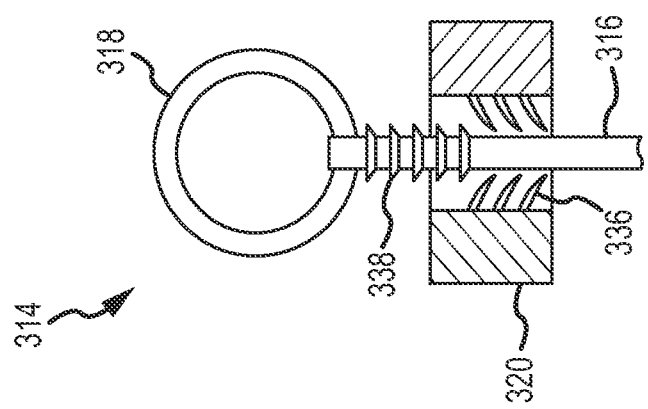

Referring to FIG. 23, an embodiment of a deployable ligation band 314 is shown that provides approximately 360 degree engagement. As shown, the deployable ligation band 314 comprises an elastomeric band 318, a tang 316, and a collar 320. The tang 316 is connected with the band 318 and is partially inserted through an opening formed in the collar 320. Locking members 336 are disposed within the collar opening and are configured to engage ridges 338 formed on the tang 316. The locking members 336 allow the ridges 338 to pass through the opening when the band 318 is being tightened, but, upon opposing motion, the locking members engage the ridges and prevent backward movement. The advantage of this embodiment is that the locking members engage the ridges around the entire perimeter of the linkage, thus providing substantially 360 degree engagement. The engagement ensures that, once deployed, the locking mechanism will maintain sufficient tension in the ligation band to block off blood flow and systemic support to a body part.

Figure 24:
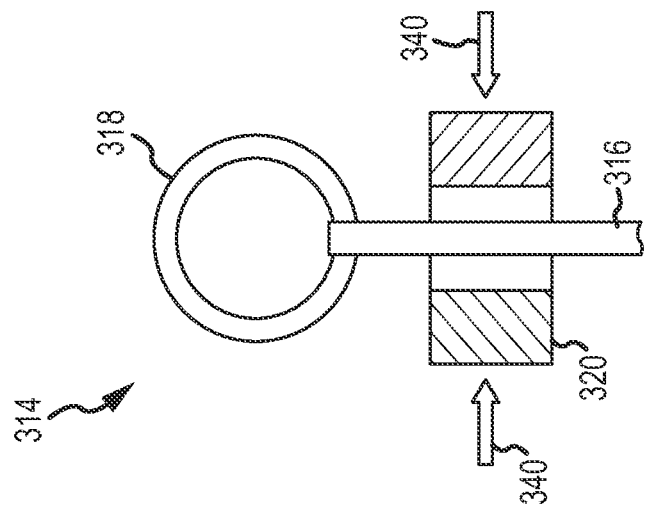

Referring to FIG. 24, an embodiment of a deployable ligation band 314 is shown that requires crimping to secure tension in a tightened band 318. As shown, the deployable ligation assembly comprises an elastomeric band 318, a tang 316, and a collar 320. The tang 316 is connected with the band 318 and is partially inserted through an opening formed in the collar 320. The collar 320 comprises a malleable material that deforms upon compression by a crimping assembly. In use, force 340 is applied to the tang 316 via a tensioning rod until a desired level of tension is applied to the band 318. Then, a crimping force is applied to at least a portion of the external surface of the collar until the collar 320 is crimped around the tang 316 and/or band 318, thereby securing tension in the band 318. After the collar 320 is crimped, the tang 316 is disconnected from the tensioning rod or tension applicator. The deployable ligation band 314 remains attached to a body part, and the tension in the ligation band blocks off blood flow and system support to the body part.

In various embodiments, ligation bands of the present invention do not require the use of an additional tool to apply the band to an animal. It will be expressly recognized, therefore, that the present invention is not limited to a ligation device or system comprising any particular application tool or, for that matter, any tool at all. Indeed, it is contemplated that ligation bands of the present invention may be applied directly to an animal and tension applied by hand. In one embodiment, a ligating band comprising self-locking features is provided such that a user may apply tension to the band in a tensioning direction and the band will not retreat or return toward or to an un-tensioned state.

The present invention, in various embodiments, includes components, methods, processes, systems and/or apparatus as depicted and described herein, including various embodiments, sub combinations, and subsets thereof. The drawings are not to scale, and various modifications to the dimensions and shapes depicted and described herein are within the scope of the present invention. Additionally, the present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations, combinations, and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of ligating an animal body part, comprising the steps of:
    providing a ligation band comprising:
        i. an elastomeric loop having a predetermined circumference;
        ii. a tang portion securely connected to the elastomeric loop for applying a tension on the loop, the tang portion comprising an aperture for receiving a tension-applying member;
        iii. a collar portion comprising an aperture for receiving the tang portion and at least a portion of the elastomeric loop, the collar portion comprising first and second locking members in the form of angles walls on opposing sides of the aperture and extending rearwardly toward the tang portion, the first and second locking members sized to securely engage a portion of the loop and allow for single-directional movement of the loop with respect to the collar portion when the portion of the loop is translated through the aperture and to secure a tension applied to the loop;
    providing a ligation device in force-transmitting communication with the ligation band;
    expanding the elastomeric loop around a portion of the ligation device;
    placing the expanded elastomeric loop around a body part to be ligated;
    applying a force to the ligation device and returning the elastomeric loop to a non-expanded state;
    applying a tension to the elastomeric loop via tensioning of the tang portion, wherein the tension applied to the elastomeric loop is maintained by the first and second locking members; and
    removing the ligation device and allowing the ligation band to remain in contact with the body part to be ligated.

2. The method of claim 1, wherein at least one of the first and second locking members comprises a plurality of teeth for securely engaging a portion of the loop.

3. The method of claim 1, wherein each of the first and second locking members comprise a plurality of teeth for securely engaging a portion of the loop.

4. The method of claim 1, wherein the tang portion comprises a length of substantially non-elastic material having a first end and a second end.

5. The method of claim 1, further comprising applying a crimping force to the elastomeric loop to secure a tension of the elastomeric loop.

6. The method of claim 1, wherein the method of ligating an animal body part is devoid of incisions or cutting of the body part.

7. A method of ligating an animal body part, comprising:
    providing a ligation band comprising:
        i. an elastomeric loop having a predetermined circumference;
        ii. a tang portion securely connected to the loop for applying a tension on the loop, the tang portion comprising an aperture for receiving a tension-applying member;
        iii. a collar portion comprising an aperture for receiving the tang portion and at least a portion of the elastomeric loop, the collar portion comprising at least one protrusion sized to securely engage a portion of the loop when the portion is translated through the aperture;

providing a ligation device in force-transmitting communication with the ligation band;

placing the ligation device around a body part to be ligated;

applying a tension to the elastomeric loop and translating the elastomeric loop with respect to the collar portion and the hinged protrusion, and wherein the hinged protrusion is hingedly displaced during the translation, wherein the tension applied to the elastomeric loop is maintained by at least one of the collar portion and the hinged protrusion;

removing the ligation device and allowing the ligation band to remain in a tensioned state and in contact with the body part to be ligated.

8. The method of claim 7, wherein the ligation device comprises a hook member and wherein the hook member applies the tension to the elastomeric loop.

9. The method of claim 7, wherein the at least one protrusion comprises at least one angled wall for receiving and maintaining a tension applied to the elastomeric loop.

10. The method of claim 7, wherein the at least one hinged protrusion comprises a plurality of teeth for securely engaging a portion of said loop.

11. The method of claim 7, wherein the aperture of the collar portion comprises two or more wall portions hinged to prevent the portion of the loop from returning to an initial position after the portion is translated.

12. The method of claim 7, wherein the hinged protrusion comprises a plurality of protrusions angled to prevent the portion of the loop from returning to an initial position after the portion is translated.

13. The method of claim 7, wherein the tang portion comprises a length of substantially non-elastic material having a first end and a second end.

14. The method of claim 7, further comprising applying a crimping force to the elastomeric loop to secure a tension of the elastomeric loop.

15. The method of claim 7, wherein the method of ligating an animal body part is devoid of incisions or cutting of the body part.

16. A method of ligating an animal body part, comprising:
providing a ligation band comprising:
i. an elastomeric loop having a predetermined circumference;
ii. a tang portion securely connected to the loop for applying a tension on the loop, the tang portion comprising an aperture for receiving a tension-applying member;
iii. a collar portion comprising an aperture for receiving the tang portion and at least a portion of the elastomeric loop, the collar portion comprising at least one angled protrusion sized to securely engage a portion of the loop when said portion is translated through the aperture, at least one angled protrusion hingedly secured to the collar portion;

providing a ligation device in force-transmitting communication with at least one of the tang portion and the collar portion;

expanding the elastomeric loop, securing the elastomeric loop in an expanded state, and placing the ligation device around a body part to be ligated;

releasing the elastomeric loop from the expanded state;

applying a tension to the elastomeric loop and thereby contracting the elastomeric loop around the body part to be ligated, wherein the tension applied to the elastomeric loop is maintained by at least one of the collar portion and the protrusion;

removing the ligation device and allowing the ligation band to remain in a tensioned state and in contact with the body part to be ligated.

* * * * *